US012653559B2

(12) United States Patent
Bek

(10) Patent No.: US 12,653,559 B2
(45) Date of Patent: Jun. 16, 2026

(54) SYSTEM AND METHOD OF UNIFORMLY DELIVERING ULTRASONIC ENERGY

(71) Applicant: Otsuka Medical Devices Co., Ltd., Tokyo (JP)

(72) Inventor: Robin Bek, Campbell, CA (US)

(73) Assignee: Otsuka Medical Devices Co., Ltd., Tokyo (JP)

(*) Notice: Subject to any disclaimer, the term of this patent is extended or adjusted under 35 U.S.C. 154(b) by 447 days.

(21) Appl. No.: 18/295,175

(22) Filed: Apr. 3, 2023

(65) Prior Publication Data

US 2023/0320738 A1 Oct. 12, 2023

Related U.S. Application Data

(60) Provisional application No. 63/371,638, filed on Aug. 16, 2022, provisional application No. 63/362,558, filed on Apr. 6, 2022.

(51) Int. Cl.
*A61B 17/22* (2006.01)
*A61B 17/00* (2006.01)

(52) U.S. Cl.
CPC .................. *A61B 17/22004* (2013.01); *A61B 2017/00778* (2013.01); *A61B 2017/22005* (2013.01)

(58) Field of Classification Search
CPC .......... A61B 17/22004; A61B 17/2202; A61B 17/320068; A61B 2017/00778; A61B 2017/22005; A61B 2017/22027
USPC .......................................................... 606/27
See application file for complete search history.

(56) References Cited

U.S. PATENT DOCUMENTS

| | | | |
|---|---|---|---|
| 3,931,533 | A | 1/1976 | Raso |
| 4,554,925 | A | 11/1985 | Young |
| 4,578,650 | A | 3/1986 | Watson |
| 4,643,186 | A | 2/1987 | Rosen |
| 4,650,466 | A | 3/1987 | Luther |
| 4,709,698 | A | 12/1987 | Johnston et al. |
| 4,841,977 | A | 6/1989 | Griffith et al. |
| 4,983,169 | A | 1/1991 | Furukawa |
| 5,000,185 | A | 3/1991 | Yock |

(Continued)

FOREIGN PATENT DOCUMENTS

| | | |
|---|---|---|
| EP | 1299035 | 4/2003 |
| EP | 1503685 | 2/2005 |

(Continued)

OTHER PUBLICATIONS

Borchert, Bianca et al., “Lethal Atrioesophageal Fistual After Pulmonary Vein Isolation using High-Intensity Focused Ultrasound (HIFU)” J. Hrthm vol. 5, Issue 1, p. 145-148, Jan. 2008.

(Continued)

*Primary Examiner* — Beverly M Flanagan
(74) *Attorney, Agent, or Firm* — Theresa Ann Raymer

(57) ABSTRACT

A tissue treatment system includes a catheter and a generator. The catheter is configured to be introduced into a blood vessel. The catheter includes an ultrasound transducer disposed at a distal end portion of the catheter to emit an unfocused ultrasound energy to treat a target tissue from the blood vessel. The generator is configured to drive the ultrasound transducer with a frequency. The generator is configured to control the frequency to change during the treatment of the target tissue. Other embodiments are also described and claimed.

36 Claims, 5 Drawing Sheets

(56) References Cited

U.S. PATENT DOCUMENTS 5,114,423 A 5/1992 Kasprzyk
5,368,591 A 11/1994 Lennox
5,391,197 A 2/1995 Burdette et al.
5,423,811 A 6/1995 Imran et al.
5,558,672 A 9/1996 Edwards et al.
5,575,788 A 11/1996 Baker et al.
5,606,974 A 3/1997 Castellano
5,620,479 A 4/1997 Diederich
5,657,755 A 8/1997 Desai
5,662,124 A * 9/1997 Wilk ...................... A61B 34/20 606/7
5,685,839 A 11/1997 Edwards et al.
5,688,266 A 11/1997 Edwards et al.
5,800,482 A 9/1998 Pomeranz et al.
5,897,569 A 4/1999 Kellogg
6,050,943 A 4/2000 Slayton
6,055,859 A 5/2000 Kozuka
6,066,134 A 5/2000 Eggers et al.
6,097,985 A 8/2000 Kasevich et al.
6,117,101 A 9/2000 Diederich et al.
6,254,598 B1 7/2001 Edwards
6,283,989 B1 9/2001 Laufer et al.
6,292,695 B1 9/2001 Webster
6,296,619 B1 10/2001 Brisken et al.
6,383,151 B1 5/2002 Diederich et al.
6,514,249 B1 2/2003 Maguire et al.
6,529,756 B1 3/2003 Phan
6,564,096 B2 5/2003 Mest
6,569,109 B2 5/2003 Sakurai
6,584,360 B2 6/2003 Francischelli et al.
6,599,288 B2 7/2003 Maguire
6,607,502 B1 8/2003 Maguire
6,635,054 B2 10/2003 Fjield et al.
6,648,883 B2 11/2003 Francischelli et al.
6,669,655 B1 12/2003 Acker
6,692,490 B1 2/2004 Edwards
6,719,755 B2 4/2004 Sliwa, Jr. et al.
6,763,722 B2 7/2004 Field et al.
6,837,886 B2 1/2005 Collins
6,845,267 B2 1/2005 Harrison et al.
6,954,977 B2 10/2005 Maguire
7,052,695 B2 5/2006 Kalish
7,156,816 B2 1/2007 Schwartz et al.
7,162,303 B2 1/2007 Levin et al.
7,371,231 B2 5/2008 Rioux et al.
7,510,536 B2 3/2009 Foley et al.
7,617,005 B2 11/2009 Demarais et al.
7,621,873 B2 11/2009 Owen et al.
7,653,438 B2 1/2010 Deem et al.
7,717,948 B2 5/2010 Demarais et al.
7,942,871 B2 5/2011 Thapliyal et al.
8,024,050 B2 9/2011 Libbus et al.
8,025,688 B2 9/2011 Diederich et al.
8,137,274 B2 3/2012 Weng et al.
8,414,494 B2 4/2013 Vaezy
8,447,414 B2 5/2013 Johnson et al.
8,483,831 B1 7/2013 Hiavka et al.
8,626,300 B2 1/2014 Demarais et al.
8,702,619 B2 4/2014 Wang
8,774,913 B2 7/2014 Demarais et al.
8,790,281 B2 7/2014 Diederich et al.
8,818,514 B2 8/2014 Zarins et al.
8,845,629 B2 9/2014 Demarais et al.
8,932,289 B2 1/2015 Mayse et al.
9,022,948 B2 5/2015 Wang
9,024,507 B2 5/2015 Lewis
9,028,472 B2 5/2015 Mathur et al.
9,066,720 B2 6/2015 Ballakur et al.
9,072,902 B2 7/2015 Mathur et al.
9,155,590 B2 10/2015 Mathur
9,186,198 B2 11/2015 Demarais et al.
9,186,212 B2 11/2015 Nabulovsky et al.
9,289,132 B2 3/2016 Ghaffari
9,326,816 B2 5/2016 Srivastava
9,327,123 B2 5/2016 Yamasaki
9,333,035 B2 5/2016 Rudie
9,339,332 B2 5/2016 Srivastava
9,345,530 B2 5/2016 Ballakur et al.
9,375,154 B2 6/2016 Wang
7,717,948 C1 8/2016 Demarais et al.
9,427,579 B2 8/2016 Fain et al.
9,439,598 B2 9/2016 Shimada et al.
9,649,064 B2 5/2017 Toth et al.
9,700,371 B2 7/2017 Brewer et al.
9,707,034 B2 7/2017 Schaer
9,723,998 B2 8/2017 Wang
9,730,639 B2 8/2017 Toth et al.
9,743,845 B2 8/2017 Wang
9,750,560 B2 9/2017 Ballakur et al.
9,770,291 B2 9/2017 Wang et al.
9,770,593 B2 9/2017 Gross
9,801,684 B2 10/2017 Fain
9,820,811 B2 11/2017 Wang
9,907,983 B2 3/2018 Thapliyal et al.
9,931,047 B2 4/2018 Srivastava
9,943,666 B2 4/2018 Warnking
9,956,034 B2 5/2018 Toth et al.
9,968,790 B2 5/2018 Toth et al.
9,981,108 B2 5/2018 Warnking
9,999,463 B2 6/2018 Puryear et al.
10,004,458 B2 6/2018 Toth et al.
10,004,557 B2 6/2018 Gross et al.
10,010,364 B2 7/2018 Harringtpm
10,016,233 B2 7/2018 Pike
10,022,085 B2 7/2018 Toth et al.
10,039,901 B2 8/2018 Warnking
10,123,903 B2 11/2018 Warnking et al.
10,143,419 B2 12/2018 Toth et al.
10,179,020 B2 1/2019 Ballakur et al.
10,179,026 B2 1/2019 Ng
10,182,865 B2 1/2019 Naga et al.
10,226,633 B2 3/2019 Toth et al.
10,238,895 B2 3/2019 Sarge
10,245,429 B2 4/2019 Deem et al.
10,292,610 B2 5/2019 Srivastava
10,293,190 B2 5/2019 Zarins et al.
10,363,359 B2 7/2019 Toth et al.
10,368,775 B2 8/2019 Hettrick et al.
10,368,944 B2 8/2019 Schaer
10,376,310 B2 8/2019 Fain et al.
10,383,685 B2 8/2019 Gross et al.
10,398,332 B2 9/2019 Min et al.
10,456,605 B2 10/2019 Taylor et al.
10,470,684 B2 11/2019 Toth et al.
10,478,249 B2 11/2019 Gross et al.
10,499,937 B2 12/2019 Warnking
10,543,037 B2 1/2020 Shah
10,850,091 B2 12/2020 Zarins et al.
11,801,085 B2 10/2023 Wu et al.
2001/0023365 A1 9/2001 Medhkour et al.
2002/0042610 A1 4/2002 Sliwa, Jr. et al.
2002/0072741 A1 6/2002 Sliwa, Jr. et al.
2002/0165535 A1 11/2002 Lesh
2002/0173724 A1 11/2002 Dorando et al.
2002/0193681 A1 12/2002 Vitek et al.
2003/0004439 A1 1/2003 Pant et al.
2003/0028111 A1 2/2003 Vaezy et al.
2003/0074039 A1 4/2003 Puskas
2003/0114878 A1 6/2003 Diederich et al.
2003/0125726 A1 7/2003 Maguire et al.
2003/0181963 A1 9/2003 Pellegrino et al.
2003/0216721 A1 11/2003 Diederich et al.
2003/0216792 A1 11/2003 Levin
2004/0019349 A1 1/2004 Fuimaono et al.
2004/0082859 A1 4/2004 Schaer
2004/0097819 A1 5/2004 Duarte
2004/0106880 A1 6/2004 Weng et al.
2004/0122494 A1 6/2004 Eggers et al.
2004/0181178 A1 9/2004 Aldrich et al.
2004/0242999 A1 12/2004 Vitek et al.
2005/0038340 A1 2/2005 Vaezy et al.
2005/0159738 A1 7/2005 Visram et al.
2005/0203501 A1 9/2005 Aldrich et al.
2005/0215990 A1 9/2005 Govari

(56) References Cited

U.S. PATENT DOCUMENTS

| | | | |
|---|---|---|---|
| 2005/0228283 | A1 | 10/2005 | Gifford et al. |
| 2005/0228459 | A1 | 10/2005 | Levin et al. |
| 2005/0228460 | A1 | 10/2005 | Levin et al. |
| 2005/0261672 | A1 | 11/2005 | Deem et al. |
| 2005/0288730 | A1 | 12/2005 | Deem |
| 2006/0041277 | A1 | 2/2006 | Deem et al. |
| 2006/0052695 | A1 | 3/2006 | Adam et al. |
| 2006/0058711 | A1 | 3/2006 | Harhen et al. |
| 2006/0064081 | A1 | 3/2006 | Rosinko |
| 2006/0118127 | A1 | 6/2006 | Chinn |
| 2006/0142827 | A1 | 6/2006 | Willard et al. |
| 2006/0184069 | A1 | 8/2006 | Vaitekunas |
| 2006/0217772 | A1 | 9/2006 | Libbus et al. |
| 2006/0235286 | A1 | 10/2006 | Stone et al. |
| 2006/0273695 | A1 | 12/2006 | Savage |
| 2007/0060921 | A1 | 3/2007 | Janssen et al. |
| 2007/0072741 | A1 | 3/2007 | Robideau et al. |
| 2007/0106292 | A1 | 5/2007 | Kaplan |
| 2007/0135875 | A1 | 6/2007 | Demarais et al. |
| 2008/0039746 | A1 | 2/2008 | Hissong et al. |
| 2008/0215031 | A1 | 9/2008 | Belfort et al. |
| 2009/0228033 | A1 | 9/2009 | Babaev |
| 2009/0234407 | A1 | 9/2009 | Hastings et al. |
| 2009/0248005 | A1 | 10/2009 | Rusin et al. |
| 2011/0098573 | A1 | 4/2011 | Thorton |
| 2011/0118723 | A1 | 5/2011 | Turner et al. |
| 2011/0125206 | A1 | 5/2011 | Bornzin |
| 2011/0208096 | A1 | 8/2011 | Demarais et al. |
| 2012/0004656 | A1 | 1/2012 | Jackson et al. |
| 2012/0265198 | A1 | 10/2012 | Crow et al. |
| 2012/0296232 | A1 | 11/2012 | Ng |
| 2013/0023897 | A1 | 1/2013 | Wallace |
| 2013/0085489 | A1 | 4/2013 | Fain et al. |
| 2013/0096550 | A1 | 4/2013 | Hill |
| 2013/0116737 | A1 | 5/2013 | Edwards et al. |
| 2013/0123770 | A1 | 5/2013 | Smith |
| 2013/0131743 | A1 | 5/2013 | Yamasaki et al. |
| 2013/0150749 | A1 | 6/2013 | McLean et al. |
| 2013/0165925 | A1 | 6/2013 | Mathur et al. |
| 2013/0172872 | A1 | 7/2013 | Subramaniam |
| 2013/0274614 | A1 | 10/2013 | Shimada et al. |
| 2013/0289369 | A1 | 10/2013 | Margolis |
| 2013/0289682 | A1 | 10/2013 | Barman et al. |
| 2014/0018788 | A1 | 1/2014 | Engelman et al. |
| 2014/0058294 | A1 | 2/2014 | Gross et al. |
| 2014/0257271 | A1 | 9/2014 | Mayse et al. |
| 2014/0274614 | A1 | 9/2014 | Min et al. |
| 2014/0275924 | A1 | 9/2014 | Min et al. |
| 2014/0288551 | A1 | 9/2014 | Bharmi et al. |
| 2014/0288616 | A1 | 9/2014 | Rawat et al. |
| 2014/0303617 | A1 | 10/2014 | Shimada |
| 2015/0289931 | A1 | 10/2015 | Puryear et al. |
| 2016/0000345 | A1 | 1/2016 | Kobayashi et al. |
| 2016/0045121 | A1 | 2/2016 | Akingba et al. |
| 2017/0027460 | A1 | 2/2017 | Shimada et al. |
| 2017/0035310 | A1 | 2/2017 | Shimada et al. |
| 2017/0296264 | A1 | 10/2017 | Wang |
| 2018/0022108 | A1 | 1/2018 | Mori et al. |
| 2018/0042670 | A1 | 2/2018 | Wang et al. |
| 2018/0064359 | A1 | 3/2018 | Pranaitis |
| 2018/0078307 | A1 | 3/2018 | Wang et al. |
| 2018/0185091 | A1 | 7/2018 | Toth et al. |
| 2018/0221087 | A1 | 8/2018 | Puryear et al. |
| 2018/0249958 | A1 | 9/2018 | Toth et al. |
| 2018/0250054 | A1 | 9/2018 | Gross et al. |
| 2018/0280082 | A1 | 10/2018 | Puryear et al. |
| 2018/0289320 | A1 | 10/2018 | Toth et al. |
| 2018/0310991 | A1 | 11/2018 | Pike |
| 2018/0333204 | A1 | 11/2018 | Ng |
| 2019/0046111 | A1 | 2/2019 | Toth et al. |
| 2019/0046264 | A1 | 2/2019 | Toth et al. |
| 2019/0076191 | A1 | 3/2019 | Wang |
| 2019/0099624 | A1 | 4/2019 | Kurtz |
| 2019/0110704 | A1 | 4/2019 | Wang |
| 2019/0134396 | A1 | 5/2019 | Toth et al. |
| 2019/0151670 | A1 | 5/2019 | Toth et al. |
| 2019/0159834 | A1 | 5/2019 | Gilmour |
| 2019/0183560 | A1 | 6/2019 | Ballakur et al. |
| 2019/0307361 | A1 | 10/2019 | Hettrick et al. |
| 2020/0046248 | A1 | 2/2020 | Toth et al. |
| 2020/0077907 | A1 | 3/2020 | Shimada et al. |
| 2021/0038925 | A1 | 2/2021 | Emery |
| 2021/0196308 | A1* | 7/2021 | Inaba ............ A61B 17/320092 |

FOREIGN PATENT DOCUMENTS

| | | | |
|---|---|---|---|
| EP | 1579889 | 9/2005 | |
| EP | 1009303 B1 | 6/2009 | |
| EP | 2359764 | 8/2011 | |
| EP | 2430996 | 3/2012 | |
| EP | 1854157 B1 | 4/2014 | |
| EP | 2842604 | 3/2015 | |
| EP | 2968984 | 1/2016 | |
| EP | 2646171 B1 | 2/2016 | |
| EP | 2995250 | 3/2016 | |
| EP | 1415146 B1 | 4/2016 | |
| EP | 2520101 B1 | 3/2021 | |
| EP | 3799931 | 4/2021 | |
| WO | WO 99/02096 A1 | 1/1999 | |
| WO | WO 01/13357 A1 | 2/2001 | |
| WO | WO2001/095820 | 12/2001 | |
| WO | WO2002/005897 | 1/2002 | |
| WO | WO 2002/019934 | 3/2002 | |
| WO | WO2003/022167 | 3/2003 | |
| WO | WO2003/051450 | 6/2003 | |
| WO | WO2006/041881 | 4/2006 | |
| WO | WO2006/060053 | 6/2006 | |
| WO | WO2007/014003 | 2/2007 | |
| WO | WO-2014022716 A2 * | 2/2014 | ....... A61B 17/22012 |
| WO | WO-2022182645 A1 * | 9/2022 | ....... A61B 17/22012 |

OTHER PUBLICATIONS

Calkins, Hugh et al., "Temperature Monitoring During Radiofrequency Catheter Ablation Procedures Using Closed Loop Control," Circulation vol. 90, No. 3, p. 1279-1286, Sep. 1994.

Deardorff, Dana L. et al., "Control of interstitial thermal coagulation: Comparative evaluation of microwave and ultrasound applicators," Medical Physics vol. 28, No. 1, p. 104-117, Jan. 2001.

Dinerman, Jay L. et al., "Temperature Monitoring During Radiofrequency Ablation," Journal of Cardiovascular Electrophysiology, vol. 7 No. 2, p. 163-173, Feb. 1996.

Esler, Murray et al., "The future of renal denervation," Autonomic Neuroscience: Basic and Clinical, vol. 204, p. 131-138, May 2017.

Filonenko, E.A. et al., "Heating of Biological Tissues by Two-Dimensional Phased Arrays with Random and Regular Element Distributions," Acoustical Physics, vol. 50 No. 2, p. 222-231, 2004.

Fry, William J., "Action of Ultrasound on Nerve Tissue—A review," The Journal of the Acoustical Society of America, vol. 25 No. 1, p. 1-5, Jan. 1953.

Fry, Frank J., "Precision High Intensity Focusing Ultrasonic Machines for Surgery," High Intensity Focused U.S., 152-156, Sep. 6-7, 1957.

Haines, David, "Biophysics of Ablation: Application to Technology," Journal of Cardiovascular Electrophysiology, vol. 15, No. 10, pg. S2-S11, Oct. 2004.

Hynynen, K. et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging—Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.

Lafon, C. et al., "Design and Preliminary Results of an Ultrasound Applicator for Interstitial Thermal Coagulation," Ultrasound in

(56) References Cited

OTHER PUBLICATIONS

Medicine & Biology, vol. 24, No. 1, p. 113-122, 1998.
Lewis, Matthew A. et al., "Thermometry and Ablation Monitoring with Ultrasound," Int. J. Hyperthermia vol. 31, Issue 2, p. 163-181, Mar. 2015.
Liu, Xinmeng et al., "Visualization and mapping of the right phrenic nerve by intracardiac echocardiography during atrial fibrillation ablation," Europace vol. 25, p. 1352-1360, 2023.
Mendelsohn, Farrell O., "Microanatomy of the Renal Sympathetic Nervous System," Endovascular Today, p. 59- 62, Oct. 2013.
Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.
Quadri, Syed A. et al., "High-intensity focused ultrasound: past, present, and future in neurosurgery," Neurosurgical Focus, vol. 44, No. 2, p. 1-9, Feb. 2018.
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (SPYRAL HTN OFF-MED) and presence (SPYRAL HTN ON-MED) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. Vol. 43, No. 1, p. 217-225, 1998.
Stauffer, P.R et al., "13 Interstitial Heating Technologies," Thermoradiotherapy and Thermochemotherapy, p. 279-320, 1995.
Swanson, David K. et al., "Tissue temperature Feedback Control of Power, The Key to Successful Ablation," Innovations, vol. 6 No. 4, p. 276-282, Jul./Aug. 2011.
Tabei, Makoto et al., "A k-space method for coupled first-order acoustic propagation equations," J. Acoust. Soc. Am., vol. 111, No. 1, pt. 1, p. 53-63, Jan. 2002.
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.
Accornero, Neri et al., "Selective Activation of Peripheral Nerve Fibre Groups of Different Diameter by Triangular Shaped Stimulus Pulses", J. Physiol. (1977), 273, _ 539-560. 22 Q9S.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Appeal Brief of Patent Owner from Reexamination 95-002, 110.
Aytac, et al., "Correlation Between the Diameter of the Main Renal Artery and the Presence of an Accessory Renal Artery", J Ultrasound Med 22:433-439, 2003.
Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).
Bailey, M.R. et al., Physical Mechanisms of the Therapeutic Effect of Ultrasound (A Review), Acoustical Physics, vol. 49, No. 4, 2003, pp. 369-388.
Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.
Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.
Bhatt, D.L., et al., A Controlled Trial of Renal Denervation for Resistant Hypertension, New England J. Med., 370:1393-1401 (2014).
Bhatt, Deepak L. et al., Long-term outcomes after catheter-based renal artery denervation for resistant hypertension: final follow-up of the randomised Symplicity HTN-3 Trial, 400 Lancet 1405 (2022).
Billard, B.E. et al., Effects of Physical Parameters on High Temperature Ultrasound Hyperthermia, Ultrasound in Med. & Biol. Vol. 16, No. 4, pp. 409-420, 1990.
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).
Blanketjin, Peter, Sympathetic Hyperactivity in Chronic Kidney Disease, Neprhrol Dial Transplant, vol. 19, No. 6, 1354-1357 (2004).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, May 2001, 1041-1049 (2001).
Camasao, D. B. et al., The mechanical characterization of blood vessels and their substitutes in the continuous quest for physiological-relevant performances: A critical review, Materials Today Bio, vol. 10 (2021).
Carter, J., "Microneurography and Sympathetic Nerve Activity: A Decade-By-Decade Journey across 50 Years," Journal of Neurophysiology, vol. 121, No. 4. doi: 10.1 152/jn.00570.2018.
Carter, Stefan et al., Measurement of Renal Artery Pressures by Catheterization in Patients with and without Renal Artery Stenosis, Circulation, vol. XXXIII, 443-449 (1966).
Chapelon, J.Y., "Treatment of Localised Prostate Cancer with Transrectal High Intensity Focused Ultrasound," European Journal of Ultrasound 9, 31-38, 1999.
Charlesworth, Peter et al., Renal Artery Injury from a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Coates, Paul et al., "Time, Temperature, Power, and Impedance Considerations for Radiofrequency Catheter Renal Denervation," Cardiovascular Revascularization Medicine 42, 171-177 (2022).

(56) References Cited

OTHER PUBLICATIONS

Corrected Patent Owner's Response to Office Action, dated May 10, 2013, from File History of Inter Partes Reexamination U.S. Appl. No. 95/002,110.
Correspondence from PTAB Deputy Chief Clerk to Counsel re conference call request—Exhibit 3001 in the Patent Trial and Appeal Board, United States Patent and Trademark Office, Petition No. PTAB-IPR2022-00431.
Curriculum Vitae of Dr. Chris Daft.
Curriculum Vitae of Dr. John M. Moriarty.
Curriculum Vitae of Dr. Michael Bohm.
Curriculum Vitae of Farrell Mendelsohn.
Dangas, G., et al., Intravascular Ultrasound—Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Deardorff, Dana et al., Ultrasound Applicators with Internal Cooling for Interstitial Thermal Therapy, SPIE vol. 3594, 36-46, Jan. 1999.
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S Pat. No. 7,717,948.
Declaration of Dr. John M. Moriarty in German Nullity proceedings for EP2261905 dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner's Response, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Dibona, Gerald F., "Neural Control of the Kidney, Past, Present and Future," 41 [Part II] Hypertension 621 24 (2003).
Dibona, Gerald, Sympathetic Nervous System and Kidney in Hypertension, Current Opinion in Nephrology and Hypertension, vol. 11, 197-200 (2002).
Dibona, Gerald F. et al., "Neural Control of Renal Function", 77 Physiological Reviews No. 1, 75 (1997).
Diederich, et al., "Catheter-based Ultrasound Applicators for Selective Thermal Ablation: progress towards MRI-guided applications in prostate," International Journal of Hyperthermia, 20:7, 739-756.
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_ doi:10.1109fTBME.2002. 807323.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019—Preliminary Remarks for EP appeal No. T2680/16-3.3.4.01.
European Search Report in Application No. 12180431.4 dated Jan. 17, 2013.
European Communication in Application No. 12180431.4 dated Oct. 23, 2013.
European Office Action in Application No. 12180431.4.
European Patent No. 12167931, Claims of the Main Request dated Sep. 30, 2016.
European Search Report (Supplementary) in Application No. 14775754.6 dated Feb. 17, 2016.
European Search Report in Application No. 218186547 dated Nov. 19, 2018.
European Search Report in Application No. 20202272.9 dated Mar. 1, 2021.
Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Fengler, Karl et al., A Three-Arm Randomized Trial of Different Renal Denervation Devices and Techniques in Patients with Resistant Hypertension (RADIOSOUND-HTN), 139 Circulation 590 (2019).
File History to EP1802370B1 Part 1.
File History to EP1802370B1 Part 2.
File History to EP1802370B1 Part 3.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.

(56) References Cited

OTHER PUBLICATIONS

He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, September 1 958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S et al., Radiofrequency ablation of the kidney: acute and chronic histology in porcine model, 56 Urology 872 (2000).
Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA-Salt Hypertension in The Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, MASSDEVICE (Dec. 6, 2016).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. Oct. 10, 2003.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Lee, Jong Deok et al., MR imaging-histopathologic correlation of radiofrequency thermal ablation lesion in a rabbit liver model: observation during acute and chronic stages, 2 Korean J. Radiol. 151 (2001).
Levin, S., et al., ARDIAN: Succeeding Where Drugs Fail—Treating Hypertension in the Cath Lab, In Vivo, 27:23 (2009).
Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).
Marine, Joseph E., Catheter ablation therapy for supraventricular arrhythmias, 298 JAMA 2768 (2007).
Martin, Louis G. et al., Long-term Results of Angioplasty in 110 Patients with Renal Artery Stenosis, Journal of Vascular and Interventional Radiology, vol. 3, No. 4, 619-626 (1992).
Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.
Matsumoto, Edward D. et al., Short-term efficacy of temperature-based radiofrequency ablation of small renal tumors, 65 Urology 877 (2005).
Medtronic Press Release, Medtronic Announces U.S. Renal Denervation Pivotal Trial Fails to Meet Primary Efficacy Endpoint While Meeting Primary Safety Endpoint (Jan. 9, 2014).
Medtronic Inc., Renal Denervation (RDN): Novel Catheter-Based Treatment for Hypertension, Scientific Background, 2011.
Medtronic Scientific Background, Hypertension and the Symplicity Renal Denervation System.
Medtronic, Symplicity RDN Common System Q&A.
Medtronic Inc., The Symplicity RDN System, 2012.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Millard, et al., Renal Embolization for Ablation of Function In Renal Failure And Hypertension, Postgraduate Med. J. 65, 729-734 (1989).
Mitchell, et al., "The Renal Nerves" British Journal of Urology, Read by invitation at the Sixth Annual Meeting of the British Association of Urological Surgeons on Jun. 30, 1950.
Morrissey, D. M. "Sympathectomy in the treatment of hypertension." Lancet, CCLXIV:403-408 (1953).
Nair et al., "The Need for and the Challenges of Measuring Renal Sympathetic Nerve Activity," Heart Rhythm 2016; 13:1166-1171.
Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).
Netter, Frank, Atlas of Human Anatomy, Icon Learning Systems, Rochester, NY (2002).
Neumann, Jutta, Sympathetic hyperactivity in chronic kidney disease: Pathogenesis, clinical relevance, and treatment, International Society of Nephrology, vol. 65, 1568-1576 (2004).
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Notice of Deposition of Tucker, filed Dec. 30, 2022 in the Patent Trial and Appeal Board, United States Patent and Trademark Office, Petition No. PTAB-IPR2022-00431.
Notice of Deposition of van der Weide, filed Dec. 30, 2022 in the Patent Trial and Appeal Board, United States Patent and Trademark Office, Petition No. PTAB-IPR2022-00431.
Notice re filing date accorded, dated Feb. 10, 2022 in the Patent Trial and Appeal Board, United States Patent and Trademark Office, Petition No. PTAB-IPR2022-00431.
Nozawa, T., et al. "Effects of long-term renal sympathetic denervation on heart failure after myocardial infarction in rats." Heart Vessels, 16:51-56 (2002).
Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").
Olsson, R. et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.

(56) References Cited

OTHER PUBLICATIONS

Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.
Order Setting Oral Hearing 37 C.F.R. § 42.70, dated Mar. 24, 2023 in the Patent Trial and Appeal Board, United States Patent and Trademark Office, Petition No. PTAB-IPR2022-00431.
Osborn, J., "Catheter-Based Renal Nerve Ablation as a Novel Hypertension Therapy, Lost, and Then Found," in Translation.
Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).
Page, Irvine H. & George J. Heuer, The Effect of Renal Denervation on Patients Suffering from Nephritis, 14 J. Clinical Investigation 443 (1935) (received for publication in 1935).
Papademetriou, Vasilios et al., Renal Sympathetic Denervation for the Treatment of Difficult-to-Control or Resistant Hypertension, 2011 Int. J. Hypertension, Article 196518 (2011).
Papademetriou, et al., "Renal Sympathetic Denervation: Hibernation or Resurrection?", Cardiology 2016; 135, 11 pgs.
Papadopoulos, N., "Evaluation of a Small Flat Rectangular Therapeutic Ultrasonic Transducer Intended for Intravascular Use," Ultrasonics 74, 196-203, 2017.
Pappone C, et al., "Circumferential radiofrequency ablation of pulmonary vein ostia: a new anatomic approach for curing atrial fibrillation", Circulation. 2000; 102(21): 2619-2628. (2000).
Patent Owner's Amended Objections to Evidence Under 37 C.F.R. §42.64.
Patent Owner's Mandatory Notice, filed Feb. 3, 2022 in the Patent Trial and Appeal Board, United States Patent and Trademark Office, Petition No. PTAB-IPR2022-00431.
Patent Owner's Notice of Deposition of Dr. Chris Daft, filed Sep. 20, 2022 in the Patent Trial and Appeal Board, United States Patent and Trademark Office, Petition No. PTAB-IPR2022-00431.
Patent Owner's Notice of Deposition of Dr. Chris Daft filed Feb. 21, 2023 in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.
Patent Owner's Notice of Deposition of Dr. John Moriarty, filed Feb. 21, 2023 in the Patent Trial and Appeal Board, United States Patent and Trademark Office, Petition No. PTAB-IPR2022-00431.
Patent Owner's Objections to Evidence, filed Aug. 18, 2022 in the Patent Trial and Appeal Board, United States Patent and Trademark Office, Petition No. PTAB-IPR2022-00431.
Patent Owner's Power of Attorney, filed Feb. 3, 2022 in the Patent Trial and Appeal Board, United States Patent and Trademark Office, Petition No. PTAB-IPR2022-00431.
Patent Owner Medtronic Ireland Power of Attorney, filed May 10, 2022 in the Patent Trial and Appeal Board, United States Patent and Trademark Office, Petition No. PTAB-IPR2022-00431.
Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Purerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martinek, Martin, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications," Biological Procedures Online, Jan. 2006, 25 pages.
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Romanes, G.J., Cunningham's Textbook of Anatomy (11th ed. 1972).
Ryan, Steve, What are the Risks Associated with a Pulmonary Vein Ablation Procedure?, Atrial Fibrillation: Resources for Patients (last accessed Oct. 18, 2022).
Ryan, Thomas et al., Proceedings of Thermal Treatment of Tissue with Image Guidance, Progress in Biomedical Optics, vol. 3594 (1999).
Ryan, Thomas P., Thermal Treatment of Tissue with Image Guidance; Ultrasound Catheters For Circumferential Cardiac Ablation 1999;.

(56) References Cited

OTHER PUBLICATIONS

Sakakura, Kenichi et al., Anatomic Assessment of Sympathetic Peri-Arterial Renal Nerves in Man, Journal of the American College of Cardiology, vol. 64, No. 7, 635-643 (2014).
Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.
Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").
Sato, Yu, et al., "Translational Value of Preclinical Models for Renal Denervation: a histological comparison of human versus porcine renal nerve anatomy," EuroIntervention, 18, e1120-e1128, 2023.
Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.
Schmieder, Ronald E., Renal denervation in patients with chronic kidney disease: current evidence and future perspectives, Nephrol. Dial. Transplant. gfac189 (2022).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Schmidt, Boris, et al., "Pulmonary Vein Isolation by High Intensity Focused Ultrasound," Indian Pacing and Electrophysiology Journal, pp. 126-133 (2006).
Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Shimizu, Kazumasa et al., Sympathetic Dysfunction in Heart Failure, Bailliere's Clinical Endocrinology and Metabolism, vol. 7, No. 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Smithwick, R. H., et al., "Splanchnicectomy for essential hypertension." J. Am. Med. Assoc., 152:1501-1504 (1953).
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swartz, John F. et al., Radiofrequency Endocardial Catheter Ablation of Accessory Atrioventricular Pathway Atrial Insertion Sites, 87 Circulation 487 (1993).
Tank, J. et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07. 012.
Tanaka, Kazushi et al., "A New Radiofrequency Thermal Balloon Catheter for Pulmonary Vein Isolation," Journal of the American College of Cardiology vol. 38, No. 7, 2001.
Teigen et al., Segmental Renal Artery Embolization for Treatment of Pediatric Renovascular Hypertension, J. Vasco Interv. Radiol. 3, 111-7 (1992).
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of the Mar. 2, 2023 deposition of Dr. John Moriarty.
Transcript of the Mar. 3, 2023 deposition of Dr. Chris Daft.
Transcript of deposition of the Jan. 1, 2023 deposition of Dr. Robert Tucker.
Transcript of the Jan. 14, 2023 deposition of Dr. Daniel van der Weide.
Transcript of the Sep. 30, 2022 deposition of Dr. Chris Daft.
Transcript of the Oct. 1, 2022 deposition of Dr. Farrell Mendelsohn.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Uchida, et al., "Effect of radiofrequency catheter ablation on parasympathetic denervation: A comparison of three different ablation sites." PACE, 21 :2517-2521 (1998).
Ulmsten, Ulf et al., "The Safety and Efficacy of MenoTreatTM, a new balloon device for thermal endometrial ablation," Acta Obstet Gynecol Scand 2001; 80: 52-57.
Vaezy, Shahram et al., Image-Guided Acoustic Therapy, Annual Review Biomedical Engineering, vol. 3, 375-390 (2001).
Valente, John F. et al., Laparoscopic renal denervation for intractable ADPKD-related pain, 16 Nephrol. Dial. Transplant. 160 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wanchoo, Nishey, Medtronic Gets European and Australian Approval for Symplicity Spyral Multi-Electrode Renal Denervation Catheter, Medgadget (2013).
Weinstock, Marta et al., "Renal Denervation Prevents Sodium Retention and Hypertension in Salt-Sensitive Rabbits with Genetic Baroreflex Impairment", 90 Clinical Science 287 (1996).
Xu, J. et al., "A Bidirectional Neuromodulation Technology for Nerve Recording and Stimulation, Micromachines," vol. 9, 1 1 538. Oct. 23, 2018. doi:10.3390/mi9110538.
Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
U.S. Appl. No. 17/453,636, filed Nov. 4, 2021, File History.
U.S. Appl. No. 10/408,665, File History.
U.S. Appl. No. 60/624,793, File History.
U.S. Appl. No. 60/370,190, File History.
U.S. Appl. No. 60/415,575, File History.
U.S. Appl. No. 60/442,970, File History.
U.S. Appl. No. 60/616,254, File History.
U.S. Appl. No. 60/747,137, File History.
U.S. Appl. No. 60/808,306, File History.
U.S. Appl. No. 60/816,999, File History.
U.S. Appl. No. 61/405,472, File History.
U.S. Appl. No. 11/532,814, Non-Final Office Action mailed Mar. 29, 2012.
U.S. Appl. No. 14/683,966, Non-Final Office Action mailed Jun. 12, 2017, 14 pgs.
U.S. Appl. No. 14/683,966, Response filed Nov. 10, 2017 to Non-Final Office Action mailed Jun. 12, 2017, 13 pgs.

(56) References Cited

OTHER PUBLICATIONS

U.S. Appl. No. 14/683,966, Notice of Allowance mailed Jan. 31, 2018, 8 pgs.
U.S. Appl. No. 14/683,966, PTO Response to Rule 312 Communication mailed Mar. 29, 2018, 2 pgs.
U.S. Appl. No. 14/683,966, 312 Amendment filed Mar. 13, 2018, 10 pgs.
U.S. Appl. No. 14/683,966, Corrected Notice of Allowance mailed May 22, 2018, 4 pgs.
U.S. Appl. No. 15/204,349, Preliminary Amendment filed Nov. 30, 2016, 3 pgs.
U.S. Appl. No. 15/204,349, Restriction Requirement mailed May 17, 2018, 7 pgs.
U.S. Appl. No. 15/204,349, Response filed Jun. 5, 2018 to Restriction Requirement mailed May 17, 2018, 7 pgs.
U.S. Appl. No. 15/204,349, Non-Final Office Action mailed Nov. 27, 2018, 14 pgs.
U.S. Appl. No. 15/204,349, Response filed Feb. 27, 2019 to Non-Final Office Action mailed Nov. 27, 2018, 10 pgs.
U.S. Appl. No. 15/204,349, Final Office Action mailed Apr. 22, 2019, 16 pgs.
U.S. Appl. No. 15/204,349, Response filed Jun. 24, 2019 to Final Office Action mailed Apr. 22, 2019, 12 pgs.
U.S. Appl. No. 15/204,349, Advisory Action mailed Jul. 9, 2019, 5 pgs.
U.S. Appl. No. 15/261,732, Notice of Allowance dated Sep. 25, 2018.
U.S. Appl. No. 15/299,694, Restriction Requirement mailed Aug. 6, 2018, 6 pgs.
U.S. Appl. No. 15/299,694, Response filed Oct. 8, 2018 to Restriction Requirement mailed Aug. 6, 2018, 7 pgs.
U.S. Appl. No. 15/299,694, Non-Final Office Action mailed Nov. 27, 2018, 15 pgs.
U.S. Appl. No. 15/299,694, Non-Final Office Action mailed Nov. 27, 2018, 10 pgs.
U.S. Appl. No. 15/299,694, Final Office Action mailed Apr. 22, 2019, 16 pgs.
U.S. Appl. No. 15/299,694, Response filed Feb. 27, 2019 to Non-Final Office Action mailed Apr. 22, 2019, 11 pgs.
U.S. Appl. No. 15/299,694, Advisory Action mailed Jul. 9, 2019, 5 pgs.
U.S. Appl. No. 15/943,354, Preliminary Amendment filed Apr. 3, 2018, 9 pgs.
U.S. Appl. No. 15/943,354, Restriction Requirement mailed Nov. 20, 2019, 8 pages.
U.S. Appl. No. 15/943,354, Response filed Dec. 19, 2019 to Restriction Requirement mailed Nov. 20, 2019, 8 pages.
U.S. Appl. No. 15/943,354, Non-Final Office Action mailed Jan. 13, 2020, 6 pages.
U.S. Appl. No. 15/943,354, Non-Final Office Action mailed Apr. 20, 2020, 7 pages.
U.S. Appl. No. 15/996,978, Preliminary Amendment filed Jun. 5, 2018, 11 pages.
U.S. Appl. No. 15/996,978, Restriction Requirement mailed Feb. 7, 2020, 7 pages.
U.S. Appl. No. 15/996,978, Response filed Apr. 6, 2020 to Restriction Requirement mailed Feb. 7, 2020, 8 pages.
U.S. Appl. No. 15/996,978, Restriction Requirement mailed Apr. 16, 2020, 8 pages.
U.S. Appl. No. 15/996,978, Response filed May 1, 2020 to Restriction Requirement mailed Apr. 16, 2020, 8 pgs.
U.S. Appl. No. 15/996,978, Non-Final Office Action mailed Jun. 11, 2020, 8 pages.
U.S. Appl. No. 16/219,874, Final Office Action mailed Dec. 21, 2020, 7 pages.
U.S. Appl. No. 16/517,180, Preliminary Amendment filed Jul. 19, 2019, 12 pgs.
U.S. Appl. No. 17/453,636, filed Nov. 4, 2021.
File History of U.S. Appl. No. 12/754,337.
File History to U.S. Pat. No. 9,943,666.
File History to U.S. Pat. No. 9,981, 108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-Final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.
Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
U.S. Appl. No. 11/225,530, filed Mar. 23, 2006, Rosinko.
Gelet, A. et al., High-Intensity Focused Ultrasound Experimentation on Human Benign Prostatic Hypertrophy, European Urology, vol. 23, 44-47 (1993).
Umemura, Shin-Ichiro, Focused Ultrasound transducer for thermal treatment, International Journal of Hypothermia, vol. 31, No. 2, 216-221 (2015).
Ahmed, Muneeb et al., "Thermal Ablation Therapy for Hepatocellular Carcinoma," J. Vasc. Interv, Radiol., vol. 13, No. 9 pt. 2, 2002.
Benito, Fernando et al., "Radiofrequency catheter ablation of accessory pathways in infants," Heart, vol. 78, p. 160-162, 1997.
Chang, Isaac A. et al., "Thermal Modeling of Lesion Growth with Radiofrequency Ablation Devices," Biomedical Engineering Online vol. 3, p. 27, 2004.
Chung, Andrew et al., "Thermal dosimetry of a focused ultrasound beam in vivo by magnetic resonance imaging," Medical Physics, vol. 26, No. 9, p. 2017-2026, Sep. 1999.
Damianou, Christakis et al., "High Intensity Focused Ultrasound Ablation of Kidney Guided MRI," Ultrasound in Med. & Biol., vol. 30, No. 3, p. 397-404, 2004.
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Diederich, Chris J. et al., "Ultrasound Technology for Hyperthermia," Ultrasound in Med. & Biol., vol. 25, No. 6, p. 871-887, 1999.
Fry, F.J. et al., "Production of Reversible Changes in the Central Nervous System by Ultrasound," Science, vol. 127, p. 83-84, Jan. 1958.
Gavrilov, L.R. et al., The Effect of Focused Ultrasound on the Skin and Deep Nerve Structures of Man and Animal, p. 279-292.
Gavrilov, L.R., "Use of Focused Ultrasound for Stimulation of Nerve Structures," Ultrasonics, p. 132-138, May 1984.
Graham, S.J. et al., "Quantifying Tissue Damage Due to Focused Ultrasound Heating Observed by MRI" Magnetic Resonance in Medicine vol. 41, p. 321-328, 1999.
Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.
Häcker, Axel et al., "Extracorporeal Organotripsy for Renal Tumours," Current Opinion in Urology, vol. 13, p. 221-225, 2003.
Hausberg, Martin et al., "Sympathetic Nerve Activity in End-Stage Renal Disease," Circulation, vol. 106, p. 1974-1979, 2002.
Ho, Siew Yen et al., "Anatomy of the Left Atrium: Implications for Radiofrequency Ablation of Atrial Fibrillation," J Cardiovasc Electrophysiol, vol. 10, p. 1525-1533, Nov. 1999.
Israel, Gary M. et al., "MRI of the Kidney and Urinary Tract," Journal of Magnetic Resonance Imaging, vol. 24, p. 725-734, 2006.
Jiang, S.C. et al., "Effects of Thermal Properties and Geometrical Dimensions on Skin Burn Injuries," Burns, vol. 28, p. 713-717, 2002.

(56) References Cited

OTHER PUBLICATIONS

Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lauder, Lucas et al., "Renal Denervation in the Management of Hypertension," EuroIntervention, vol. 20, p. e467-e478, 2024.
Lele, P.P., "Effects of Focused Ultrasonic Radiation on Peripheral Nerve, with Observations on Local Heating," Experimental Neurology, vol. 8, p. 47-83,1963.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Mahfoud, Felix et al., "Device Therapy of Hypertension," Circulation Research nol. 128, p. 1080-1099, Apr. 2021.
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue vols. Using High Intensity Focused Ultrasound" Ultrasound in Med. & Biol. vol. 22 No. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Mitchell, G.A.G et al., "An Anatomical Evaluation of Operations for Hypertension," Proceedings of the Anatomical Society vol. LIV., No. 10, p. 545-560.
Mompeo, Blanca et al., "The Gross Anatomy of the Renal Sympathetic Nerves Revisited," Clinical Anatomy vol. 29, p. 660-664, Apr. 2016.
Moore, J.H. et al., "The Biophysical Effects of Ultrasound on Median Nerve Distal Latencies," Electromyogr. Clin. Neurophysiol., vol. 40, p. 169-190, 2000.
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, Jan./Feb. 1995.
Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.
Nikfarjam, Mehrdad et al., "Mechanisms of Focal Heat Destruction of Liver Tumors," Journal of Surgical Research, vol. 127, No. 2, p. 208-223, Aug. 2005.
Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.
Papademetriou, Vasilios et al., "Renal Nerve Ablation for Resistant Hypertension, How Did We Get Here, Present Status, and Future Directions," Circulation, No. 129, p. 1440-1451, 2014.
Pozzoli, Alberto et al., "Electrophysiological Efficacy of Epicor High-Intensity Focused Ultrasound," European Journal of Cardio-Thoracic surgery, vol. 42, p. 129-134, 2012.
Riis, Thomas et al., "Effective Ultrasonic Stimulation in Human Peripheral Nervous System," IEE Transactions on Biomedical Engineering, vol. XX, No. XX, p. 1-8, XXXX 2021.
Roux, N. et al., "The Myocardial Sleeves of the Pulmonary Veins: Potential Implications for Atrial Fibrillation," Surg. Radiol. Anat., vol. 26, p. 285-289, Feb. 2004.
Schuarte, Patrick et al., "Catheter Ablation of Cardiac Autonomic Nerves for Prevention of Vagal Atrial Fibrillation," Circulation vol. 102, p. 2774-2780, 2000.
Tellez, Armando et al., "Renal Artery Nerve Distribution and Density in the Porcine Model: Biologic Implications for the Development of Radiofrequency Ablation Therapies," Translational Research vol. 162 No. 6, p. 381-389, Dec. 2013.
Ter Haar, G., "Ultrasound Focal Beam Surgery," Ultrasound in Med. & Biol., vol. 21, No. 9, p. 1089-1100, 1995.
Ter Haar, G.R. et al., "Ultrasonic Heating of Mammalian Tissues In vivo," Br. J. Cancer vol. 45, Supp. V., p. 65-67, 1982.
Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.
Trippodo, Nick C. et al., "Similarities of Genetic (Spontaneous) Hypertension," Circulation Research vol. 48, No. 3, p. 309-319, Mar. 1981.
Urban, Bruce A. et al., "Three-dimensional Volume-rendered CT Angiography of the Renal Arteries and Veins: Normal Anatomy, Variants, and Clinical Applications," RG vol. 21 no. 2, p. 373-386, Mar.-Apr. 2001.
Wang, Shyh-Hau et al., "Effects of Low Intensity Ultrasound on the Conduction Property of Neural Tissues," IEEE International Ultrasonics, Ferroelectrics, and Frequency Control Joint 50$^{th}$ Anniversary Conference, p. 1824-1827, 2004.
Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.
Wells, P.N.T., "Functional Modification: Clinical Applications," Biomedical Ultrasonics, p. 470-504, 1977.
Winternitz, Sherry R. et al., "Importance of the Renal Nerves in the Pathogenesis of Experimental Hypertension," Hypertension (supp. III), vol. 4, No. 5, pg. III-08-III-115, Sep.-Oct. 1982.
Wulff, V.J. et al., "Effects of Ultrasonic Vibrations on Nerve Tissues," P.S.E.B.M., vol. 76, p. 361-366, 1951.
Yarmolenko, Pavel S. et al., "Thresholds for thermal damage to normal tissues: An update," Int. J. Hyperthermia, vol. 27 No. 4, p. 320-343, Jun. 2011.
Young, Robert R. et al., "Functional Effects of Focused Ultrasound on Mammalian Nerves," Science, vol. 134, p. 1521-1522, Nov. 1961.
Zimmer, J.E. et al., "The Feasibility of Using Ultrasound for Cardiac Ablation," IEEE Transactions on Biomedical Engineering, vol. 42, No. 9, p. 891-897, Sep. 1995.

* cited by examiner

SYSTEM AND METHOD OF UNIFORMLY DELIVERING ULTRASONIC ENERGY

This application claims the benefit of priority of U.S. Provisional Patent Applications Nos. 63/362,558, filed on Apr. 6, 2022 and 63/371,638, filed on Aug. 16, 2022, which are incorporated herein by reference in their entirety to provide continuity of disclosure.

BACKGROUND

Field

This application relates generally to systems and methods of delivering energy to a targeted anatomical location of a subject, and more specifically, to systems configured to deliver ultrasonic energy to treat tissue, such as nerve tissue.

Background Information

According to the Centers for Disease Control and Prevention (CDC), about one in every three adults suffer from high blood pressure, also known as hypertension. Left untreated, hypertension can result in renal disease, arrhythmias and heart failure. In recent years, the treatment of hypertension has focused on minimally invasive interventional approaches to inactivate the renal nerves surrounding the renal artery. Autonomic nerves tend to follow blood vessels to the organs that they innervate. Catheters may reach specific structures that may be proximate to the lumens in which they travel. For example, one system employs a radio frequency (RF) generator connected to a catheter having multiple electrodes placed against the intima of the renal artery, which are used to create an electrical field in the vessel wall and surrounding tissue that results in resistive (ohmic) heating of the tissue to a temperature sufficient to ablate the tissue and the renal nerve passing through that tissue. To treat all the renal nerves surrounding the renal arteries, the RF electrodes are repositioned several times around the inside of the renal artery. However, the relatively confined electric fields created by the RF electrodes may miss some of the renal nerves, leading to an incomplete treatment. Additionally, to heat the renal nerves, the RF electrodes must contact the intima, posing a risk of damage or necrosis to the intima, which in turn can lead to thrombus formation, fibrosis of the vessel wall, mechanical weakening of the vessel and possible vessel dissection.

U.S. Pat. Nos. 9,943,666, 9,981,108, and 10,039,901 to Warnking, U.S. Pat. Nos. 9,700,372, 9,707,034, and 10,368,944 to Schaer, and U.S. Pat. Nos. 10,350,440 and 10,456,605 to Taylor, the entire contents of each of which is incorporated by reference herein, disclose a system that uses unfocused ultrasound to ablate nerves. Embodiments of the system include an ultrasound transducer positioned along a distal end of a catheter designed to be inserted into a blood vessel (e.g., the renal artery). Electrical cabling, which is received within a cabling lumen of the catheter, can be used to power the ultrasound transducer. The ultrasound transducer emits one or more therapeutic doses of unfocused ultrasound energy, which heats the tissue adjacent to the body lumen within which the transducer is disposed. The system may also include a balloon mounted at the distal end of the catheter used to circulate cooling fluid both prior to, during, and after activation of the transducer to cool the transducer and help prevent thermal damage to the interior surface of the blood vessel wall while the nerves are being heated and damaged at depth. Circulation of the cooling fluid occurs through two fluid lumens—an input fluid lumen that carries fluid distally to the balloon, and an output fluid lumen that returns fluid proximally from the balloon.

Such a design enables creation of one or more ablation zones sufficient to achieve long-term nerve inactivation at different locations around the circumference of the blood vessel, thereby treating a patient's hypertension while mitigating damage to the blood vessel and surrounding organs.

SUMMARY

Existing tissue treatment systems include generators. The generators drive a transducer at a single frequency to produce and deliver energy, e.g., RF or ultrasonic energy, to surrounding tissue. Driving the transducer at the single frequency generates ultrasonic lobes that are localized and spaced apart over a length of the transducer. These discrete and separated lobes can contribute to inconsistent heating of the tissue, and potentially to suboptimal treatment. For example, in the case of renal denervation treatments, the nerves may be inconsistently ablated. Accordingly, tissue treatment systems that deliver ultrasonic energy more uniformly, e.g., in a less localized manner, to surrounding tissue are needed.

A tissue treatment system is provided herein. The tissue treatment system can include components, such as an input device and one or more processors, to perform a method of delivering ultrasonic energy to surrounding tissue. For example, one or more processors can execute instructions stored on a non-transitory computer readable medium to cause the tissue treatment system to perform the method.

In an embodiment, the tissue treatment system includes an input device configured to receive, from a catheter, data representing a target frequency at which an ultrasonic transducer mounted on a distal end of the catheter optimally emits unfocused ultrasonic energy during use. The tissue treatment system includes one or more processors configured to determine, based on the target frequency, a range of frequencies. The one or more processors are configured to drive the ultrasonic transducer over the range of frequencies.

In an embodiment, the method performed by the tissue treatment system includes receiving, from a catheter, data representing a target frequency at which an ultrasonic transducer mounted on a distal end of the catheter optimally emits unfocused ultrasonic energy during use. The method includes determining, based on the target frequency, a range of frequencies. The method includes driving the ultrasonic transducer over the range of frequencies.

In an embodiment, the non-transitory computer readable medium stores instructions, which when executed by one or more processors of a tissue treatment system, causes the tissue treatment system to perform a method including receiving, from a catheter, data representing a target frequency at which an ultrasonic transducer mounted on a distal end of the catheter optimally emits unfocused ultrasonic energy during use. The method includes determining, based on the target frequency, a range of frequencies. The method includes driving the ultrasonic transducer over the range of frequencies.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Figure 1:
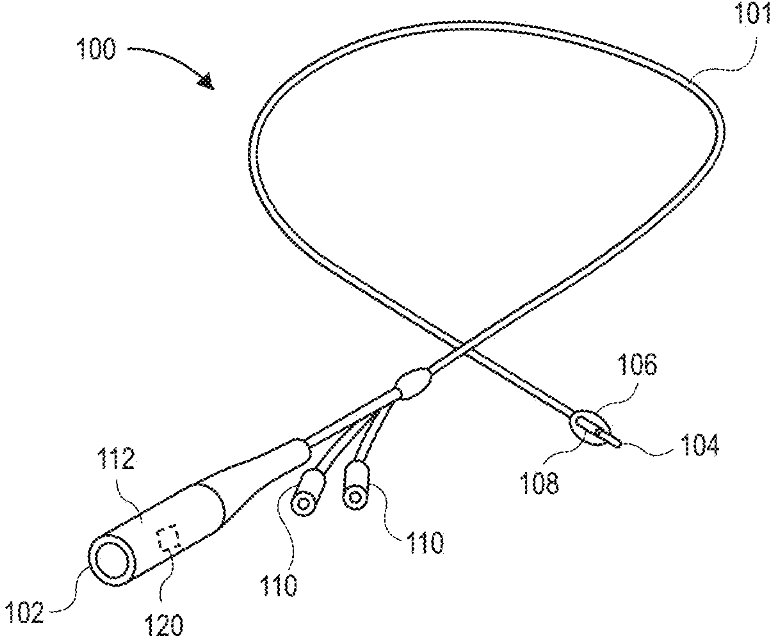
FIG. 1 is a perspective view of a catheter of a tissue treatment system, in accordance with an embodiment.

Embodiments describe a tissue treatment system having a generator and a fluid transfer cartridge, and methods of using the tissue treatment system. The tissue treatment system may be an ultrasound-based tissue treatment system, used to delivery unfocused ultrasonic energy radially outwardly to treat tissue within a target anatomical region, such as the renal nerves within a renal artery. Alternatively, the tissue treatment system may be used in other applications, such as to treat sympathetic nerves of the hepatic plexus within a hepatic artery. In other embodiments, the tissue treatment system may be used to denervate the sympathetic nerves of the splenic artery, celiac trunk, superior and/or inferior mesenteric artery. In certain embodiments, the tissue treatment catheter is used to ablate nerve fibers in the celiac ganglion and/or renal arteries to treat hypertension. In certain embodiments, the transducers are used to treat pain, such as pain associated with pancreatic cancer, by, e.g., neuromodulating nerves that innervate the pancreas. the tissue treatment system may also be used to ablate nerves of both the pulmonary vein and the renal arteries to treat atrial fibrillation. In still other examples, the tissue treatment system may additionally or alternatively be used to ablate nerves innervating a carotid body in order to treat hypertension and/or chronic kidney disease. Thus, reference to the system as being a renal denervation system, or being used in treating, e.g., neuromodulating, renal nerve tissue is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction relative to a component. Similarly, "proximal" may indicate a second direction relative to the component, opposite to the first direction. Such terms are provided to establish relative frames of reference, however, and are not intended to limit the use or orientation of tissue treatment system components, e.g., a catheter or a generator, to a specific configuration described in the various embodiments below.

In an aspect, a tissue treatment system for performing a medical procedure, e.g., a renal ablation catheterization, is provided. The tissue treatment system includes a generator to drive an ultrasonic transducer of a catheter to deliver unfocused ultrasonic energy to target vessel tissue. The transducer can be driven over a frequency range based on a target frequency. More particularly, the target frequency can be encoded in a memory feature of the catheter, and data representing the target frequency can be received by the generator and processed to determine two or more frequencies through which the generator can drive the transducer during use. When driven over the range of frequencies, e.g., by dithering about the target frequency, the transducer emits several standing lobes at different longitudinal locations that combine to form one or more energy lobes. The energy lobe(s) are wide and closely-spaced, and can cover a substantial portion of an outer surface of the transducer. Furthermore, the standing lobes may individually have eccentric emission profiles, but in combination the profiles can form a concentric, e.g., circular, emission profile of the energy lobe. Accordingly, the tissue treatment system can emit energy lobes that are more uniformly distributed longitudinally and radially relative to a central axis of the transducer as compared to, for example, energy lobes emitted by the transducer driven at a single frequency. The more uniform delivery of ultrasonic energy can achieve consistent heating of the target vessel tissue and/or the nerves therein.

Referring to FIG. 1, a perspective view of a catheter-based intraluminal device of a tissue treatment system is shown in accordance with an embodiment. The catheter-based intraluminal device of a tissue treatment system 100 can include a catheter 101 having an elongated catheter body extending from a proximal catheter end 102 to a distal catheter end 104. An expandable member 106, such as a balloon, may be mounted on the catheter 101 at the distal catheter end 104. One or more ultrasonic transducers 108 may be positioned within the expandable member 106. The expandable member 106 can be adapted to inflate within a target anatomy, e.g., a renal artery. For example, water may be flowed into and/or through the expandable member 106 to cause the expandable member to inflate. The transducer(s) 108 may therefore be water-backed transducer(s), being positioned within the water during member inflation. The energy transducer can be adapted to deliver ablation energy, e.g., ultrasonic energy, to the target anatomy during a medical procedure, e.g., a renal denervation procedure. In another embodiment, the transducer(s) 108 can be air-backed. Air-backed transducers have an air layer at the inner surface of the transducer or piezoelectric component. The air layer may help direct all acoustic energy transmitted through the outer surface or outer diameter of the transducer. Embodiments of the air-backed transducers herein can provide good uniformity and efficiency of energy to the treated tissue site and safer treatment. The uniformity of the lesion may rely on the concentricity of the piezoelectric transducer and less so on the support members that are separated from the lead zirconate titanate (PZT) member by the air layer. As such, the dependency on the transducer assembly process can be reduced without sacrificing the uniformity of acoustic field. Air in the back of the transducer, next to the inner surface of the PZT member, can ensure that the acoustic waves are launched from the outer diameter (OD) of the transducer.

The catheter 101 can include one or more lumens, such as: fluid lumens to deliver an inflation/cooling fluid to the expandable member 106, electrical cable passageways containing electrical cables to deliver energy to the transducer, guidewire lumens for exchanging guidewires, etc. The lumen(s) may be connected to corresponding connectors at the proximal catheter end 102. For example, the fluid lumens may connect to one or more fluid ports 110, which receive inflation/cooling fluid from a circulation device of the tissue treatment system 100, as described below. Similarly, the electrical cables can connect to an external connector 112, which receives energy from an ultrasonic source of the tissue treatment system 100, as described below.

In an embodiment, the catheter 101 includes a memory element 120 storing information about, representing, or related to a target range of frequencies or a target frequency of the catheter 101. For example, the information may include data related to the target frequency, such as a coefficient that is used to determine the target frequency. The information may include a target range of frequencies including several frequencies to drive the transducer, as described below. The target range of frequencies may include an upper and a lower frequency of the range, for example. In an embodiment, the target frequency may be one of the several frequencies stored, or within the target range of frequencies stored. More particularly, the memory element 120, which may be a digital memory element 120, such as an erasable programmable read-only memory (EPROM) chip, a barcode label, or another non-volatile memory component can store data representing the target frequency. The memory element 120 is shown as being integrated within the external connector 112, but it will be appreciated that the memory element 120 can be located anywhere on or in the catheter 101, including at or near the distal end 104 of the catheter 101.

The target frequency can be a frequency at which the ultrasonic transducer 108 mounted on the distal end 104 of the catheter 101 optimally emits unfocused ultrasonic energy during use. The term unfocused, as used herein, refers to an ultrasonic energy beam that does not increase in intensity in the direction of propagation of the beam away from the transducer. The target frequency can be within an operating frequency of the transducer. For example, the transducer can be configured to operate at a frequency of one to several tens of MHz, and the target frequency can be within the operational range. The target frequency can be a single frequency, e.g., 9 MHz.

Figure 2:
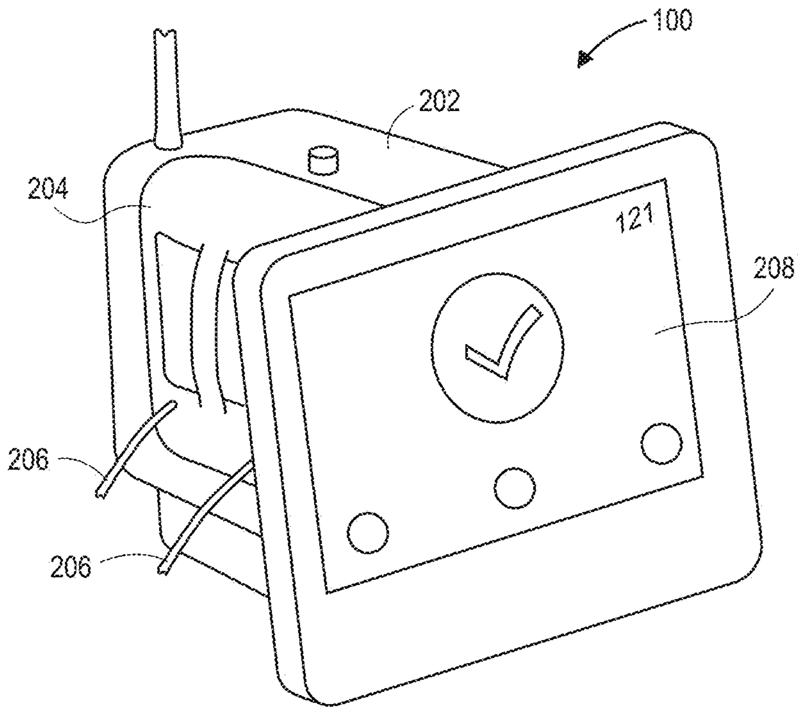
FIG. 2 is a front perspective view of a generator of a tissue treatment system, in accordance with an embodiment.

Referring to FIG. 2, a front perspective view of a generator of a tissue treatment system is shown in accordance with an embodiment. The tissue treatment system 100 includes a control unit that connects to the catheter 101 to regulate the inflation of the balloon with inflation/cooling fluid and to manage the delivery of ultrasonic energy to the transducer. In an embodiment, the control unit includes a generator 202 to generate the ultrasonic energy, and a fluid transfer cartridge 204 to transfer cooling fluid to and from the balloon through one or more fluid conduits 206. The control unit includes several other components, some of which are described below, to facilitate the energy and fluid transfer functions. Such components can include a display 208 to present procedural information to a user. Furthermore, as described with respect to FIG. 3, the control unit can include one or more processors configured to execute instructions stored by a non-transitory computer readable medium to cause the tissue treatment system 100 to perform various operations of the method of treating tissue of a target vessel, as described below.

Figure 3:
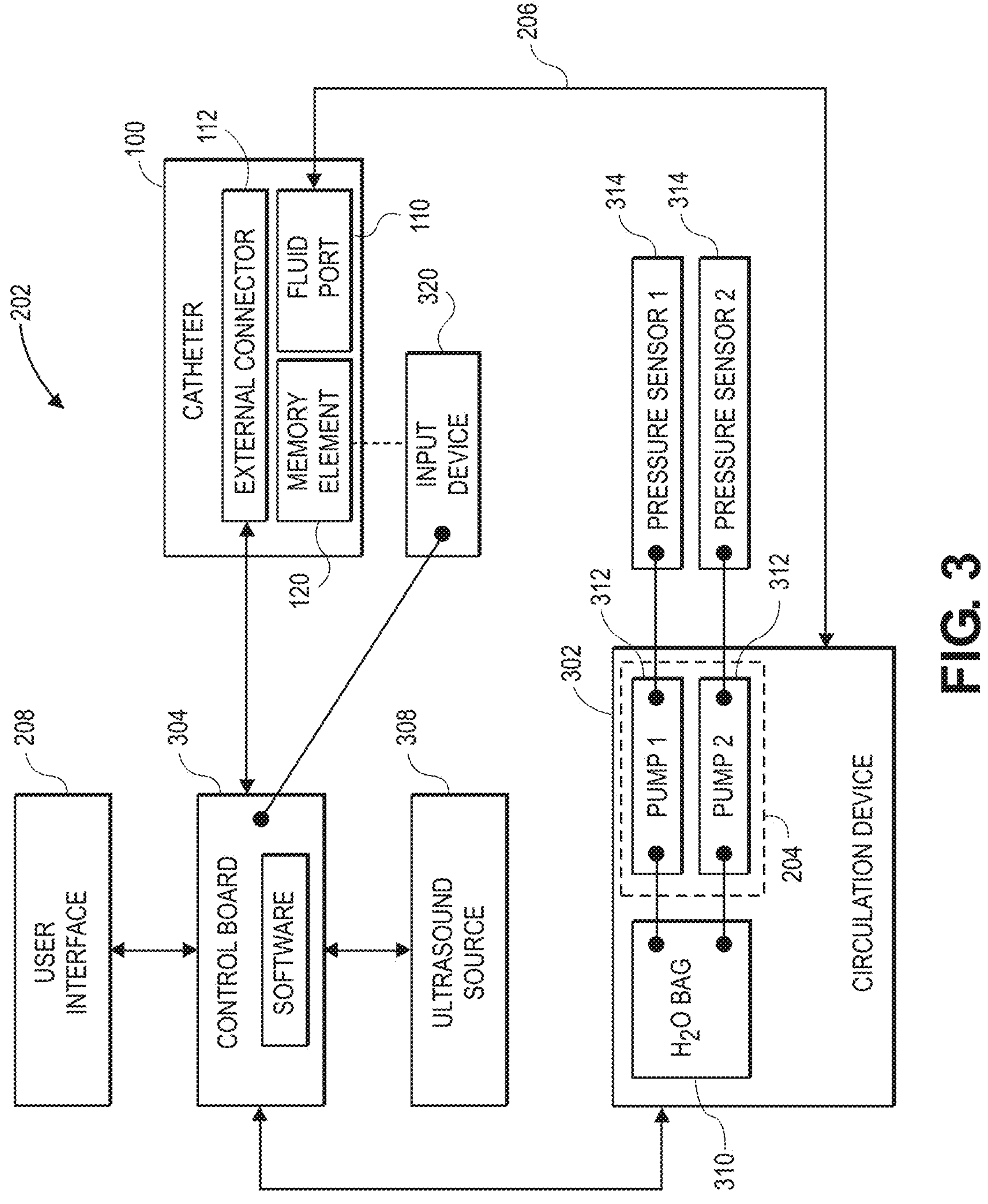
FIG. 3 is a block diagram of a generator of a tissue treatment system, in accordance with an embodiment.

Referring to FIG. 3, a block diagram of a generator of a tissue treatment system is shown in accordance with an embodiment. The generator 202 can connect to the catheter 101 during use. For example, the generator 202 may include a socket connector that receives the external connector 112 of the catheter 101, e.g., via one or more electrical lines. Similarly, a circulation device 302 of the generator 202 can connect to the fluid port 110 of the catheter 101, e.g., via the one or more fluid conduits 206. The circulation device 302 can include the fluid transfer cartridge 204.

The generator 202 may include the user interface 208. The user interface 208 can interact with a control board 304 having one or more processors, and the control board 304 can interact with an ultrasonic excitation source 308 to cause transmission of electrical signals at the target frequency of the transducer to the transducer via cables. The control board 304 and ultrasonic excitation source 308 are arranged to control the amplitude and timing of the electrical signals so as to control the power level and duration of the ultrasonic signals emitted by the transducer.

The circulation device 302 is connected to the balloon through lumens of the catheter 101. More particularly, the catheter 101 can have a shaft that includes one or more lumens to transfer fluid from the proximal catheter end 102 to the distal catheter end 104. Accordingly, the circulation device 302 can circulate a liquid, such as an aqueous liquid, through the catheter 101 to the transducer 108 in the balloon 106. The circulation device 302 may include a fluid reservoir 310 for holding the liquid and one or more pumps 312 to convey the liquid from the fluid reservoir 310 to the fluid conduit 206. In an embodiment, the circulation device 302 includes a refrigeration coil to cool the liquid being conveyed and transferred to an interior space of the balloon. The liquid can be at or below body temperature.

The control board 304 interfaces with the circulation device 302 to control the conveyance of fluid into and out of the balloon. For example, the control board 304 may include motor control devices linked to drive motors for controlling the speed of operation of the pumps 312. Such motor control devices can be used, for example, when the pumps 312 are positive displacement pumps, such as peristaltic pumps. Alternatively or additionally, the control circuit may include structures such as controllable valves connected in the fluid circuit for varying resistance of the circuit to fluid flow (not shown). The generator 202 may further include one or more pressure sensors 314 to monitor the liquid flow through the catheter 101. One pressure sensor 314 can monitor the flow of the liquid to the distal catheter end 104 of the catheter 101 to determine if there is a blockage while the other can monitor leaks in the catheter 101. While the balloon 106 is in an inflated state, the pressure sensors 314 can maintain a desired pressure in the balloon.

In an embodiment, the generator 202 includes an input device 320 to receive data from the catheter 101. For example, the input device 320 can be a scanner to read a barcode, wires to engage memory locations in an EPROM, etc. The input device 320 may therefore be configured to receive, from the catheter 101, the data representing the target frequency. More particularly, the input device 320 can receive the data from the memory element 120. The received data can be conveyed to the one or more processors of the generator 202, and used to perform the method described below.

Figure 4:
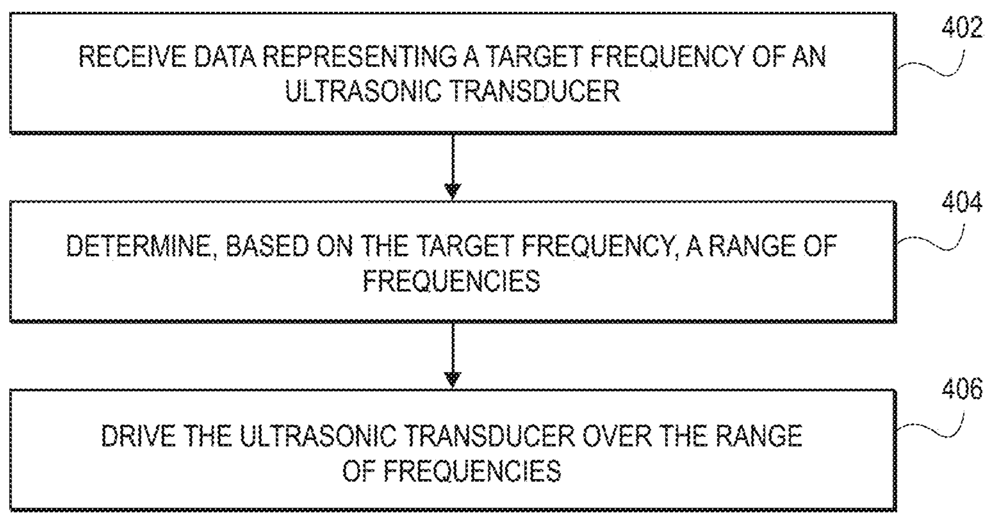
FIG. 4 is a flowchart of a method of delivering ultrasonic energy from an ultrasonic transducer, in accordance with an embodiment.

Referring to FIG. 4, a flowchart of a method of delivering ultrasonic energy from an ultrasonic transducer is shown in accordance with an embodiment. The method can cause a more uniform operation of the transducer. Transducer uniformity can be a measure of how consistently energy is generated and delivered to surrounding tissue. For example, when disposed within a vessel lumen, the transducer can deliver energy into tissue of the vessel wall in a longitudinal and circumferential direction, e.g., fully 360 degrees over a length of the transducer. Energy delivered to each location circumferentially around the vessel from a more uniform transducer will be more consistent than energy delivered to each location circumferentially around the vessel from a less uniform transducer.

At operation 402, one or more processors of the generator 202 receive data representing the target frequency of the ultrasonic transducer 108. For example, the generator 202 can receive data related to the target frequency, such as a coefficient that can be used to determine the target frequency. The target frequency can be near, but different than, a parallel resonance frequency of the ultrasonic transducer 108. For example, the target frequency can be within 1% of, but different than, the parallel resonance frequency. The parallel resonance can be a single frequency, e.g., 9 MHz. When the generator 202 is driven at the parallel resonance frequency, ultrasonic energy can be generated by the transducer and delivered to a vessel wall. The target frequency may, however, be some other desired frequency related to the resonance of the transducer. In an embodiment, the target frequency is a frequency, other than the parallel resonance frequency, at which the transducer generates energy optimally or nearly optimally. More particularly, driving the transducer at the frequency other than the series resonance frequency can be easier, from an amplifier perspective, than driving the transducer at series resonance. Series resonance means a very low impedance, which can be difficult for an amplifier to drive. Furthermore, driving the transducer at series resonance may make it harder to have consistent output because slight changes in frequency could change transducer performance. Accordingly, the target frequency can be a frequency that is easier to drive, from an amplifier perspective, and provides consistent output from the transducer.

At operation 404, the one or more processors can determine, based on the received data, a range of frequencies. The range of frequencies can be derived from the target frequency, or may be directly determined from the data, e.g., the data may include the range of frequencies. The range of frequencies can include a set of frequencies that encompasses the target frequency. For example, the range of frequencies may be 1-11% of the fundamental or carrier frequency, and may be distributed about the target frequency. When the target frequency is 9 MHz, the range of frequencies can be 8.7-9.3 MHz, 8.0-10.0 MHz, or another set containing the target frequency. The target frequency may be a median or an average of the range of frequencies. More particularly, the range of frequencies may be distributed evenly (centered about the target frequency as described above) or unevenly (e.g., 8.9-9.4 MHz in a +/−2% embodiment), relative to the target frequency. In an embodiment, the range of frequencies is a range that is +/−1% of the target frequency. The range of frequencies can be determined based on a frequency response of the transducer. More particularly, the impedance versus frequency can be monitored to determine the range of frequencies to drive the transducer.

Figure 5:
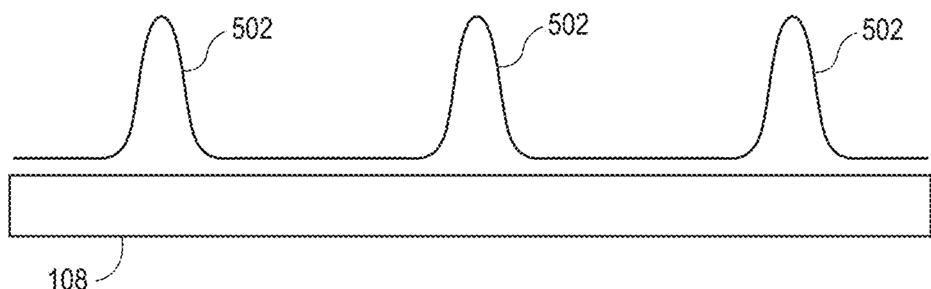
FIG. 5 is a side view of energy lobes of ultrasonic energy being emitted by an ultrasonic transducer, in accordance with an embodiment.
Figure 6:
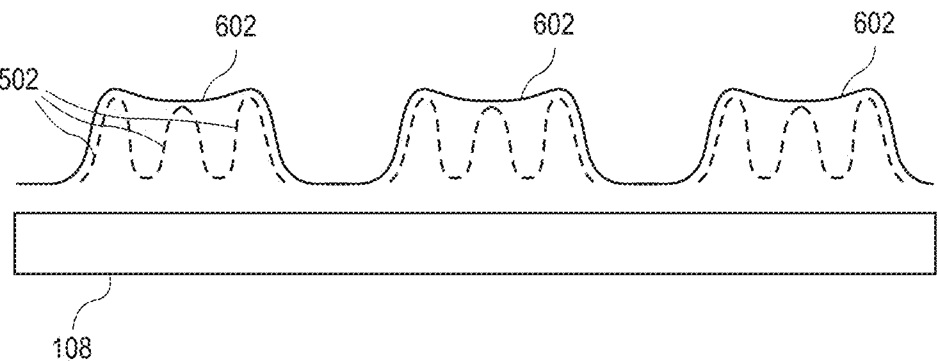
FIG. 6 is a side view of energy lobes of ultrasonic energy being emitted by an ultrasonic transducer, in accordance with an embodiment.
Figure 7:
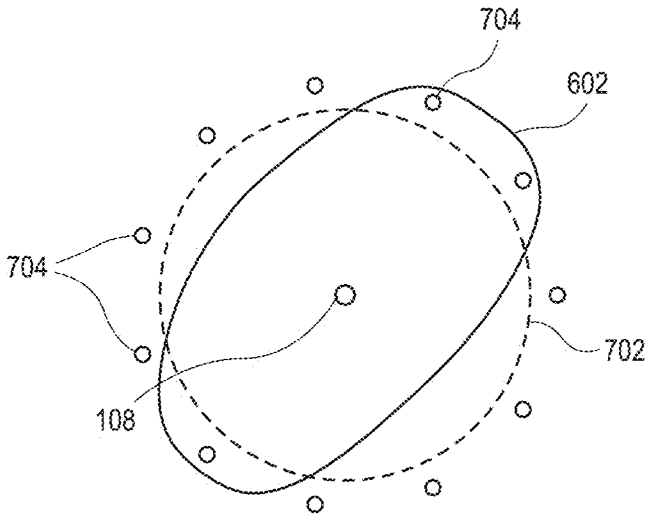
FIG. 7 is an end view of energy lobes of ultrasonic energy being emitted by an ultrasonic transducer, in accordance with an embodiment.
Figure 8:
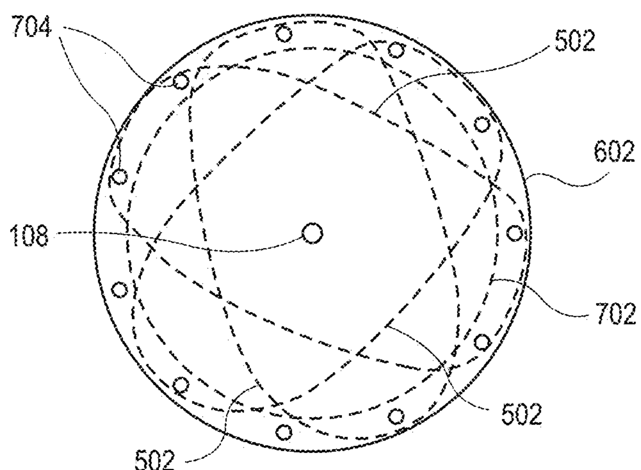
FIG. 8 is an end view of energy lobes of ultrasonic energy being emitted by an ultrasonic transducer, in accordance with an embodiment.

At operation 406, the one or more processors of the generator 202 control the ultrasonic source to drive the ultrasonic transducer 108 over the range of frequencies. The operations of the method of FIG. 4 can be used in several embodiments. For example, the transducer can be driven over a narrow range of frequencies or over a broader range of frequencies. The embodiment having the narrow range is illustrated in FIGS. 5 and 7. The embodiment having the broader range is illustrated in FIGS. 6 and 8. Accordingly, the operations of FIG. 4 shall be understood as encompassing the embodiments described below.

Referring to FIG. 5, a side view of energy lobes of ultrasonic energy being emitted by an ultrasonic transducer is shown in accordance with an embodiment. When the ultrasonic transducer 108 is driven over the range of frequencies, ultrasonic energy may still be emitted by the transducer in several, e.g., three, energy lobes 502. The lobes 502 may, however, appear to be wider than when the transducer is driven over a single frequency. The energy lobes 502 can be less discretely located and spaced apart from each other over a length of the transducer.

The illustrated lobes are represented by an amplitude of energy delivery shown at longitudinal locations along an outer surface of the transducer. When the transducer is driven over a narrow range of frequencies, individual standing lobes can be localized at a same location along the transducer. For example, the narrow lobes of FIG. 5 may result from actuating the transducer using a tightly grouped range of frequencies, e.g., a range of frequencies within +/−0.1-1% of the target frequency.

Referring to FIG. 6, a side view of energy lobes of ultrasonic energy being emitted by an ultrasonic transducer is shown in accordance with an embodiment. Rather than driving the transducer at a single or narrow range of frequencies, the generator 202 may drive the transducer over a range of frequencies that are associated with different standing lobes along the transducer. The wider lobes of FIG. 6 may result from actuating the transducer using a broader range of frequencies, e.g., a range of frequencies within +/−0.1-11% of the target frequency. For example, the generator 202 can drive the transducer over a range of 8.9-10.0 MHz to generate distributed lobes. This range is provided by way of example, however, and other ranges may be used, such as 7.2-7.3 MHz, 8.7-8.8 MHz, or other ranges.

The standing lobes can occur at different locations along the outer surface of the transducer. The generator 202 can drive the ultrasonic transducer 108 by sweeping the ultrasound source through the range of frequencies. For example, the ultrasound source can sweep back and forth between a minimum frequency of the range of frequencies and a maximum frequency of the range of frequencies. The range of frequencies can be distributed about the target frequency, and accordingly, the generator 202 can dither about the target frequency set point to sweep through the range of frequencies. More particularly, driving the ultrasonic transducer 108 can include dithering about the target frequency within the range of frequencies.

When viewed in a time-averaged manner, the standing lobes 502 propagate back and forth along the outer surface of the transducer within the envelope of the energy lobe 602. More particularly, the standing lobes sweep back and forth over the transducer as different portions of the transducer are driven at different frequencies. The standing lobes may have respective positions on the transducer surface, and the range of frequencies may be such that at least two of the standing lobes do not overlap in longitudinal position. For example, as shown in FIG. 6, the standing lobes may include a leftmost lobe and a rightmost lobe that do not have overlapping tails. Similarly, in the illustrated case, the standing lobes include a middle lobe that does not positionally overlap with either the leftmost lobe or the rightmost lobe. Accordingly, the energy lobes 502 would appear to lengthen, or widen, as represented in FIG. 6 because the energy lobes 502 include several non-overlapping standing lobes. Furthermore, as the energy lobes 502 widen, the gaps between the lobes decreases and the energy lobes 502 become less localized and are nearer to each other. As a result, the energy lobes 502 would appear to cover more of the longitudinal surface area of the outer surface of the transducer, as compared to energy lobes caused by a narrower range of frequencies.

The standing lobes 502 are illustrated on a transverse plane extending upward from one side of the transducer, however, it will be appreciated that the lobes may actually be swept around a central axis of the transducer. More particularly, the energy lobes 502 may have the shape of rings, e.g., annular lobes, extending around the central axis. Some rings could be at a higher or lower energy levels than adjacent rings. The combined rings, and the overall energy delivery, however, can be an average of all of the adjacent rings. Accordingly, the annular standing lobes can combine to form annular energy lobes 502 that are closely-spaced and distributed over the outer surface of the transducer.

Driving the ultrasonic transducer 108 over the range of frequencies can provide more uniform heating of the vessel wall, as compared to driving the ultrasonic transducer 108 a single frequency. Delivering energy with localized, spaced apart lobes, can heat the vessel wall in discrete areas. The heat must then conductively transfer to reach other areas of the vessel wall between the discrete areas. For example, the portion of the vessel wall along the gaps between the energy lobes 502 may be heated conductively, rather than by sonication. Conductive heating, however, may not reach as deep into the vessel tissue and may be too shallow for effective nerve treatment in some areas. By contrast, widening the energy lobes 502 longitudinally, and reducing the gaps between energy lobes 502, can apply energy through closely-spaced lobes. The closely-spaced lobes may heat more of the vessel by sonication (rather than conductively), and the target tissue may be heated more uniformly. The vessel can therefore be more consistently heated to an effective depth.

Referring to FIG. 7, an end view of energy lobes of ultrasonic energy being emitted by an ultrasonic transducer is shown in accordance with an embodiment. In addition to increasing longitudinal uniformity, the method can also increase circumferential uniformity of energy delivery into the vessel wall. Given that the lobes are located at specific locations, irregularities in the transducer structure at those locations, e.g., machined grooves, roughnesses, nicks, etc., can interfere with the lobes and result in non-uniform delivery in a transverse plane. Such non-uniformities can also be caused by inconsistencies in the piezoelectrical properties of the transducer.

When the transducer 108 is disposed within a target vessel 702 and actuated to ablate a nerve 704 running through tissue surrounding a vessel lumen, the energy lobe 602 can be emitted radially outward from the transducer 108. The energy lobe 602 may, however, be biased toward a particular direction as an eccentric emission profile rather than being evenly distributed in a more concentric emission profile about a longitudinal axis of the transducer 108. This may particularly be the case when the transducer is driven over a narrow range of frequencies. As described above, the standing lobe(s) 502 in such case can be localized, and thus, any eccentricity in the emission profile caused by the transducer structure or material may be amplified. The spacing of the lobes 502 and their inconsistency in the transverse direction can result in energy not being uniformly delivered to the vessel wall. Accordingly, the vessel wall may not experience uniform or optimal heating. For example, some nerves 704 may be heated and others may not be. Nonetheless, it will be appreciated that driving the transducer 108 over a narrow range of frequencies may provide greater uniformity than driving the transducer at a single frequency.

Referring to FIG. 8, an end view of energy lobes of ultrasonic energy being emitted by an ultrasonic transducer is shown in accordance with an embodiment. By driving the transducer 108 over a wider range of frequencies, e.g., +/−0.1-11% of the target frequency, and spreading out the energy lobes 602 as described above, the ultrasonic energy is emitted more uniformly in the radial direction (in addition to being more uniform in the longitudinal direction). The uniformity with the present disclosure would spread the lobes more evenly across the transducer. More particularly, when the lobes 602 cover more of the transducer length, the vessel wall can be more consistently heated in the circumferential direction.

Circumferential uniformity of the emitted radiation may result from the wider lobes 602 covering more area of the transducer 108 such that it is less likely that standing lobes 502 will be located at surface imperfections that distort the emission profile in a same manner. Several adjacent rings will be produced that have varying levels of uniformity, and those varying levels of uniformity will provide a net average uniformity that should be more consistent. More particularly, given that each of the three standing lobes 502 illustrated in FIG. 8 would be located at different locations of the transducer, which likely have different imperfections, the average emission profile of the energy lobe 602 may be more circular. That is, the eccentric profiles of each standing lobe 502 average to form a concentric profile of the energy lobe 602. Accordingly, the energy delivery in the transverse direction may be more optimal, e.g., more concentric. The more optimal energy delivery can consistently deliver ultrasonic energy to the blood vessel wall and result in more uniform and more optimal heating of the vessel tissue. For example, all or most of the nerves 704 around the vessel lumen may be heated.

Dithering about a set point, e.g., the target frequency, can be implemented in the generator 202 according to several embodiments. More particularly, a component of the generator 202 may be configured to drive the ultrasonic transducer 108 over the range of frequencies, and the component may be controlled by the one or more processors.

In an embodiment, a piezoelectric crystal is configured to drive the ultrasonic transducer 108. The piezoelectric crystal can be integrated into the generator 202, and can cause the ultrasound source to dither about the set point, e.g., the target frequency. More particularly, the generator 202 can include a crystal that determines a frequency that the power amplifier drives to, and the crystal can be controlled by one or more processors to dither about the set point provided by the memory of the catheter 101. Accordingly, the generator 202 can drive the transducer 108 over the range of frequencies that results in more uniform energy lobes 602 (energy lobes distributed across a greater area of the transducer), as compared to standing lobes 502.

The piezoelectric crystal may be part of a spread-spectrum crystal oscillator (SSXO). The SSXO can synthesize from and modulate the frequency of an input crystal. The SSXO can allow for flexible selection of output frequency, modulation rate, and speed ratios.

In an embodiment, a voltage controlled oscillator is configured to drive the ultrasonic transducer 108. The voltage controlled oscillator can be integrated into the generator 202, and can cause the ultrasound source 108 to dither about the set point, e.g., the target frequency. A ramp signal can be applied as a voltage to the oscillator to change the frequency of the oscillator. The voltage controlled oscillator causes the generator 202 to dither within the frequency range, and results in more uniform energy lobes 602 (energy lobes that are distributed across a greater area of the transducer). The voltage controlled oscillator can be an RC oscillator, or multi vibrator type, or LC oscillator, or crystal oscillator type. The voltage controlled oscillator may be a harmonic oscillator or a relaxation oscillator.

As described above, the tissue treatment system 100 can generate ultrasonic lobes that spread out across the length of the transducer. More particularly, several adjacent rings of increased uniformity can be created because the energy is delivered across a greater area of the transducer. The broader frequency of energy delivery can allow for a more uniform ablation. Broader energy lobes 602 can deliver energy more uniformly to the vessel wall and over a greater area, resulting in more consistent heating of the target tissue. The broader frequency of energy delivery can compensate for irregularities in the transducer, which could be due to the mechanical dimensions, material properties, or piezo-electrical properties, of the transducer.

The uniformity described above can be quantified by a transducer uniformity test. Such a test can determine whether the transducer 108 can effectively deliver energy evenly across the treatment area. The test can characterize how evenly acoustic energy is distributed around the transducer 108 during transducer activation. In an embodiment, a hydrophone and a 2D scanning system can be used to scan acoustic pressure distribution around the transducer 108. The system can compute a spatial-average-temporal-average intensity (Isata) of each angle around the transducer 108, and can output a ratio between a minimum and maximum Isata. The transducer 108 can be rotated while the hydrophone is moved axially across the transducer to produce a pressure map plotting pressure generated by the transducer at each axial location along the transducer. The pressure map corresponds to acoustic energy delivered into the target vessel around the transducer 108 during ablation.

Data generated using the techniques described with respect to FIGS. 5 and 6 above indicates that driving the transducer 108 at a single or narrow range of frequencies energy lobes 502 that generate respective pressure nodes. The pressure nodes produced by energy lobes 502 are sequentially located approximately every 2 mm along the transducer. More particularly, the pressure nodes are mapped as high-pressure zones having pressures of at least 0.25 MPa, which are approximately 1 mm wide. Furthermore, the pressure nodes corresponding to energy lobes 502 have widths of less than 1.5 mm, e.g., 1 mm. By contrast, low-pressure zones located between the high-pressure zones of the pressure nodes are approximately 1 mm wide and have acoustic pressures below 0.25 MPa. Accordingly, the narrow energy lobes 502 can produce discrete pressure zones having substantially varying levels of pressure in the vessel surrounding the transducer 108.

Performing a transducer uniformity test while driving the transducer 108 over a wider range of frequencies can produce more uniform levels of pressure in the vessel surrounding the transducer. For example, test data has shown that sonication in the vessel using energy lobes 602 can generate pressure nodes having pressures of at least 0.25 MPa and widths of at least 1.5 mm. The pressure nodes corresponding to respective energy lobes 602 can be high-pressure zones in the pressure map. The high-pressure zones have pressures that are greater than 0.25 MPa. Furthermore, the width of each zone having such minimum pressure is at least 1.5 mm. Accordingly, the high-pressure zones are closely spaced. More particularly, the high-pressure zones are separated by low-pressure zones having pressures below 0.25 MPa, however, the low-pressure zones are less than 0.5 mm wide, e.g., 0.2 mm wide at most. Accordingly, the wide energy lobes 602 can produce consistently high levels of pressure in the vessel surrounding the transducer 108 during use. More particularly, the pressure nodes produced by energy lobes 602 may be spaced apart from each other by no more than 0.5 mm, and each pressure node can have a pressure of at least 0.25 MPa.

Based on the uniformity measures described above, an aspect ratio of high-pressure zones to low-pressure zones produced by the transducer 108 may be defined. More particularly, based on the uniformity test data, high-pressure nodes produced by energy lobes 602 can have widths of at least 1.5 mm and are separated by 0.5 mm or less (narrower low-pressure nodes). Accordingly, a minimum aspect ratio of high-pressure zones to low-pressure zones can be 3. Wider high-pressure zones and/or narrower low-pressure zones can increase the aspect ratio. For example, when the pressure map includes high-pressure nodes of 2 mm width and low-pressure nodes of 0.2 mm width, the aspect ratio can be 10.

It will be appreciated that the ultrasonic transducer 108 will have a quality factor (Q), which defines the sensitivity of the transducer to changes in driving frequency. Essentially, the Q of the transducer defines the width of the frequency range that will cause vibration of a particular scale. It will be appreciated, then, that a transducer 108 having a high Q will have a maximum ultrasonic output when driven at a resonant frequency. More particularly, for several transducers having a same resonant frequency, the transducer having a higher Q will output more ultrasonic energy when driven at the resonant frequency than the transducer having a lower Q. However, a bandwidth at which the lower Q transducer outputs sufficient energy to cause tissue ablation will be wider than the bandwidth at which the higher Q transducer can sufficiently ablate tissue.

Importantly, because the clinically effective bandwidth of the higher Q transducer is narrower than the lower Q transducer, in practice the higher Q transducer may have to be driven so close to the resonant frequency that standing lobes remain localized, e.g., overlapping. More particularly, the range of frequencies over which the higher Q transducer can be driven to obtain effective tissue ablation may be so narrow that the energy lobe 602, rather than being widened, is effectively the same as standing lobes generated at a single frequency, e.g., the resonant frequency of the transducer. Counterintuitively, rather than incorporating a transducer that has a narrow energy output bandwidth around the target frequency, which is beneficial in many applications, the catheter 101 can incorporate a transducer that has a broad energy output bandwidth. More particularly, the transducer can have a Q that is less than a predetermined Q to allow dithering about the target frequency with sufficient range that the energy lobe 602 can be widely distributed, as described above.

In an embodiment, the transducer has a Q less than 90. For example, the Q of the transducer may be between 60-80. The transducer having such a low Q may be referred to as a broadband transducer. By way of example, the Q of the broadband transducer can be 70, and in such case, the transducer may dither about the target frequency within +/−0.1-1% of the target frequency, as described above. Although a transducer having Q of 70 may perform suboptimally at the target frequency as compared to, e.g., a transducer having a Q of 90 or greater, the transducer having Q of 70 may nonetheless perform better at frequencies substantially higher or lower than the target frequency. Accordingly, the transducer having a Q less than 90, e.g., in a range of 60-80, can develop energy lobes 602 that are distributed over a length of the transducer, as described above. The distributed energy lobes 602 may deliver ultrasonic energy more uniformly to achieve consistent heating of the target vessel tissue and/or the nerves 704 therein.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A tissue treatment system, comprising:

a catheter configured to be introduced into a blood vessel and including an ultrasound transducer disposed at a distal end portion of the catheter to emit an unfocused ultrasound energy by emitting several standing lobes at different longitudinal locations to treat a target tissue from the blood vessel; and a generator configured to drive the ultrasound transducer with a frequency, wherein the generator is configured to control the frequency to change during the treatment of the target tissue, wherein the standing lobes combine to form one or more energy lobes.

2. The tissue treatment system of claim 1, wherein the generator is configured to control the frequency to sweep about a parallel resonance frequency of the ultrasound transducer.

3. A tissue treatment system, comprising:

an input device configured to receive, from a catheter, data representing a target frequency at which an ultrasonic transducer mounted on a distal end of the catheter emits unfocused ultrasonic energy during use; and one or more processors configured to determine, based on the data, a range of frequencies, and drive the ultrasonic transducer over the range of frequencies, wherein the catheter emits unfocused ultrasonic energy by emitting several standing lobes at different longitudinal locations, and wherein the standing lobes combine to form one or more energy lobes.

4. The tissue treatment system of claim 3, wherein the target frequency is a parallel resonance frequency of the ultrasonic transducer.

5. The tissue treatment system of claim 3, wherein driving the ultrasonic transducer includes sweeping through the range of frequencies.

6. The tissue treatment system of claim 3, wherein driving the ultrasonic transducer includes dithering about the target frequency within the range of frequencies during treatment.

7. The tissue treatment system of claim 6, wherein dithering about the target frequency includes driving the ultrasonic transducer within a range of +/−0.1-10% of the target frequency.

8. The tissue treatment system of claim 7, wherein dithering about the target frequency includes driving the ultrasonic transducer within a range of +/−1-2% of the target frequency.

9. The tissue treatment system of claim 3 further comprising a piezoelectric crystal configured to drive the ultrasonic transducer over the range of frequencies.

10. The tissue treatment system of claim 3 further comprising a voltage controlled oscillator configured to drive the ultrasonic transducer over the range of frequencies.

11. The tissue treatment system of claim 3, wherein the ultrasonic transducer is a water-backed transducer, wherein the data represents a range of frequencies, and wherein the target frequency is within the range of frequencies.

12. The tissue treatment system of claim 3, wherein the ultrasonic transducer is an air-backed transducer, wherein the data represent a range of frequencies, and wherein the target frequency is within the range of frequencies.

13. The tissue treatment system of claim 3, wherein the ultrasonic transducer has a quality factor less than 90.

14. The tissue treatment system of claim 3, wherein the one or more energy lobes are distributed longitudinally and radially relative to a central axis of the ultrasonic transducer, and wherein the one or more energy lobes generate respective pressure nodes having pressures of at least 0.25 MPa and widths of at least 1.5 mm.

15. A method of treating tissue of a target vessel, comprising:

receiving, from a catheter, data representing a target frequency at which an ultrasonic transducer mounted on a distal end of the catheter emits unfocused ultrasonic energy during use;

determining, based on the target frequency, a range of frequencies; and driving the ultrasonic transducer over the range of frequencies to emit several standing lobes at different longitudinal locations that combine to form one or more energy lobes.

16. The method of claim 15, further comprising applying energy through closely-spaced lobes to produce ablation around a circumference of a blood vessel, wherein the lobes spread out across the ultrasonic transducer, wherein the closely-spaced lobes generate a plurality of pressure nodes spaced apart from each other by no more than 0.5 mm, each pressure node having a pressure of at least 0.25 MPa.

17. The method of claim 15, wherein the target frequency is a parallel resonance of the ultrasonic transducer.

18. The method of claim 15, wherein driving the ultrasonic transducer includes sweeping through the range of frequencies.

19. The method of claim 15, wherein driving the ultrasonic transducer includes dithering about the target frequency within the range of frequencies during treatment.

20. The method of claim 19, wherein dithering about the target frequency includes driving the ultrasonic transducer within a range of +/−0.1-11% of the target frequency.

21. The method of claim 19, wherein dithering about the target frequency includes driving the ultrasonic transducer within a range of +/−0.1-1% of the target frequency.

22. The method of claim 15, wherein the ultrasonic transducer is a water-backed transducer, wherein the data represents the range of frequencies, and wherein the target frequency is within the range of frequencies.

23. The method of claim 15, wherein the ultrasonic transducer is an air-backed transducer, wherein the data represents the range of frequencies, and wherein the target frequency is within the range of frequencies.

24. The method of claim 15, wherein the ultrasonic transducer has a quality factor less than 90.

25. A non-transitory computer readable medium storing instructions, which when executed by one or more processors of a tissue treatment system, causes the tissue treatment system to perform a method comprising:

receiving, from a catheter, data representing a target frequency at which an ultrasonic transducer mounted on a distal end of the catheter emits unfocused ultrasonic energy during use;

determining, based on the target frequency, a range of frequencies; and driving the ultrasonic transducer over the range of frequencies to emit several standing lobes at different longitudinal locations that combine to form one or more energy lobes.

26. The non-transitory computer readable medium of claim 25, further comprising applying energy through closely-spaced lobes to produce ablation around a circumference of a blood vessel, wherein the closely-spaced lobes generate a plurality of pressure nodes spaced apart from each other by no more than 0.5 mm, each pressure node having a pressure of at least 0.25 MPa.

27. The non-transitory computer readable medium of claim 25, wherein the target frequency is a parallel resonance of the ultrasonic transducer.

28. The non-transitory computer readable medium of claim 25, wherein driving the ultrasonic transducer includes sweeping through the range of frequencies.

29. The non-transitory computer readable medium of claim 25, wherein driving the ultrasonic transducer includes dithering about the target frequency within the range of frequencies during treatment.

30. The non-transitory computer readable medium of claim 29, wherein dithering about the target frequency includes driving the ultrasonic transducer within a range of +/−0.1-11% of the target frequency.

31. The non-transitory computer readable medium of claim 29, wherein dithering about the target frequency includes driving the ultrasonic transducer within a range of +/−0.1-1% of the target frequency.

32. The non-transitory computer readable medium of claim 25, wherein the ultrasonic transducer is a water-backed transducer, wherein the data represents a range of frequencies, and wherein the target frequency is within the range of frequencies.

33. The non-transitory computer readable medium of claim 25, wherein the ultrasonic transducer is an air-backed transducer, wherein the data represents a range of frequencies, and wherein the target frequency is within the range of frequencies.

34. The non-transitory computer readable medium of claim 25, wherein the ultrasonic transducer has a quality factor less than 90.

35. A method of treating tissue of a target vessel, comprising:

receiving, from a catheter, data representing a target frequency at which an ultrasonic transducer mounted on a distal end of the catheter emits unfocused ultrasonic energy during use;

determining, based on the target frequency, a range of frequencies; and driving the ultrasonic transducer over the range of frequencies; and applying energy through closely-spaced lobes to produce ablation around a circumference of a blood vessel, wherein the lobes spread out across the ultrasonic transducer, wherein the closely-spaced lobes generate a plurality of pressure nodes spaced apart from each other by no more than 0.5 mm, each pressure node having a pressure of at least 0.25 MPa.

36. A non-transitory computer readable medium storing instructions, which when executed by one or more processors of a tissue treatment system, causes the tissue treatment system to perform a method comprising:

receiving, from a catheter, data representing a target frequency at which an ultrasonic transducer mounted on a distal end of the catheter emits unfocused ultrasonic energy during use;

determining, based on the target frequency, a range of frequencies;

driving the ultrasonic transducer over the range of frequencies; and applying energy through closely-spaced lobes to produce ablation around a circumference of a blood vessel, wherein the closely-spaced lobes generate a plurality of pressure nodes spaced apart from each other by no more than 0.5 mm, each pressure node having a pressure of at least 0.25 MPa.

* * * * *